United States Patent
Manabe et al.

(10) Patent No.: US 7,488,819 B2
(45) Date of Patent: Feb. 10, 2009

(54) MULTIDENTATE LIGAND

(75) Inventors: Toshio Manabe, Kawasaki (JP); Fumio Takei, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 543 days.

(21) Appl. No.: 10/940,648

(22) Filed: Sep. 15, 2004

(65) Prior Publication Data

US 2005/0054849 A1 Mar. 10, 2005

Related U.S. Application Data

(63) Continuation of application No. PCT/JP03/03086, filed on Mar. 14, 2003.

(30) Foreign Application Priority Data

| Mar. 15, 2002 | (JP) | ............................ 2002-073369 |
| Jun. 19, 2002 | (JP) | ............................ 2002-179143 |
| Sep. 30, 2002 | (JP) | ............................ 2002-288108 |

(51) Int. Cl.
C07D 245/00 (2006.01)
C07D 487/00 (2006.01)

(52) U.S. Cl. ........................................ 540/472

(58) Field of Classification Search .................. None
See application file for complete search history.

(56) References Cited

U.S. PATENT DOCUMENTS

2001/0027252 A1 10/2001 Kobuke et al.

FOREIGN PATENT DOCUMENTS

| JP | 62-065384 | 3/1987 |
| JP | 11-266007 | 9/1999 |
| JP | 2000-086684 | 3/2000 |
| JP | 2000-516273 | 12/2000 |
| WO | WO98/06242 | 2/1998 |

OTHER PUBLICATIONS

Eidman et. al., 2006, Trifluoroacetic Acid, Encyclopedia of Reagents for Organic Synthesis, pp. 1-12.*
Salmon et. al., 2001, Oxalyl Chloride, Encyclopedia of Reagents for Organic Synthesis, pp. 1-8.*
Klaubert et. al., 1981, Journal of Medicinal Chemistry, vol. 24, pp. 742-748.*

(Continued)

Primary Examiner—James O Wilson
Assistant Examiner—Jeffrey H Murray
(74) Attorney, Agent, or Firm—Staas & Halsey LLP

(57) ABSTRACT

A multidentate ligand includes at least two planar tetradentate coordination sites in one plane, each of the planar tetradentate coordination sites containing four nitrogen-containing groups of at least one of imino, amido and amino groups, and has the nitrogen atoms of the four nitrogen-containing groups as coordinating atoms in one plane. A metal complex assembly has one of two-dimensional and three-dimensional structures and contains metal complex chains and electroconductive wires, the metal complex chains each contain assembled metal complexes, the electroconductive wires each contain molecules serving as at least one of an acceptor and a donor, and the metal complex chains intersect with the electroconductive wires at such positions that the metal complexes and the molecules serving as at least one of an acceptor and a donor are capable of interacting with each other.

16 Claims, 15 Drawing Sheets

OTHER PUBLICATIONS

Official Communication from European Patent Office in corresponding European Patent Application 03 708 621.2-1211 on Mar. 19, 2007.

Deng, Yongqi et al., "Facile Synthesis of β-Derivatized Porphyrins-Structural Characterization of a β- β-Bis-Porphyrin," Angew. Chem. Int. Ed. 2000, vol. 39, No. 6, pp. 1066-1068.

Mueller, Reinhardt et al., "Derivatives of Tetraaza [14] Annulene and their Precursors. 2) Bicyclic Compounds and Polymeric Substances," Makromol. Chem., 1976, vol. 177, No. 8, pp. 2241-2258.

Fleischer, E. B. et al., "A Novel Bicyclic Octadentate Ligand which Allows the Incorporation of Two Metal Ions," Inorg. Nucl. Chem. Letters, 1973, vol. 9, pp. 1061-1067.

J. H. Schön et al., "Superconductivity in Molecular Crystals Induced by Charge Injection," Nature, 2000, vol. 406, pp. 702-704.

V. Balzani et al., "Photochemistry and Photophysics of Coordination Compounds: An Extended View," Coordination Chemistry Reviews 171, 1998, pp. 3-16.

T. M. Rice et al., "Superconductivity, Spin Gaps and Luttinger Liquids in a Class of Cuprates," Europhysics Letters, 23 (6), 1993, pp. 445-449.

M. Uehara et al. "Superconductivity in the Ladder Material $Sr_{0.4}Ca_{13.6}Cu_{24}O_{41.84}$," Journal of the Physical Society of Japan, 1996, vol. 65, No. 9, pp. 2764-2767.

N. Kimizuka et al., "Self-Assembling Molecular Wires of Halogen-Bridged Platinum Complexes in Organic Media. Mesoscopic Supramolecular Assemblies Consisting of a Mixed Valent Pt (II)/Pt (IV) Complex and Anionic Amphiphiles," Inorg. Chem., 2000, vol. 39, pp. 2684-2689.

H. Imai et al., "Molecular Spin Ladder in the $Ni(dmit)_2$ (dmit=1,3-dithiol-2-thione-4,5-dithiolate) salt with a nitronyl nitroxide cation," Physical Review B, 1996, vol. 54, No. 10, pp. 6838-6840.

James R. Heath et al., "A Defect—Tolerant Computer Architecture: Opportunities for Nanotechnology," Science, 1998, vol. 280, pp. 1716-1721.

W. Huang et al., "Molecular Ladders with Macrocyclic Platforms," Inorg. Chem., 2001, vol. 40, pp. 1712-1715.

Office Action, Nov. 13, 2007, Japan.

Reinhardt Müller wt al., "Tetraaza [14] annulen—Derivate und ihre Vorstufen, 3 Katalyse, Halbleitereigenschaften und Thermostabiliatät der Metallkomplexe", Makromaol, Chem., 1978, vol. 179, No. 9, pp. 2161-2172.

* cited by examiner

Pd(en)2

Ni(chxn)2

FIG. 2A
FIG. 2B
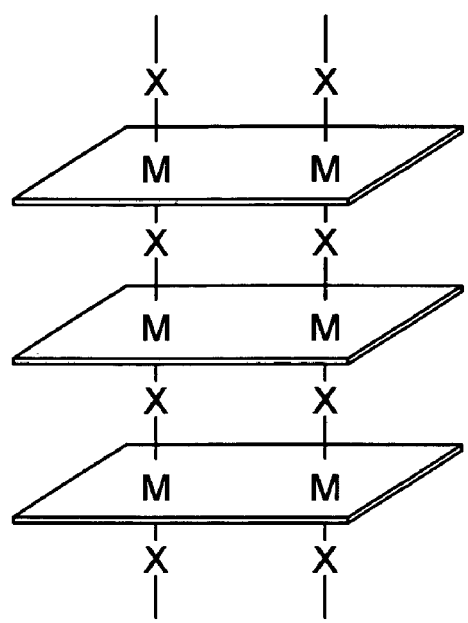
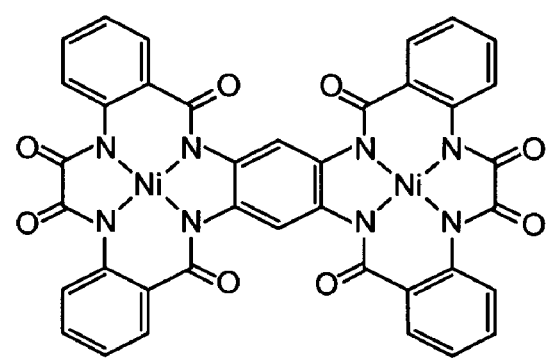
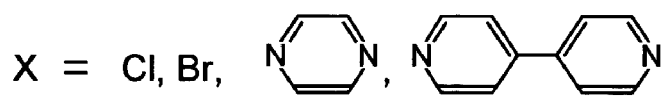

FIG. 10A
FIG. 10B
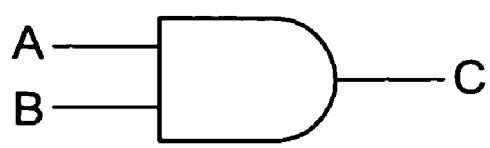
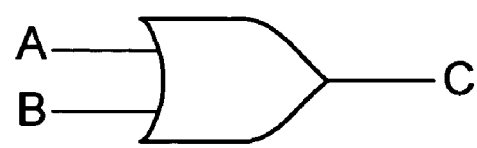
| A | B | C |
|---|---|---|
| 0 | 0 | 0 |
| 0 | 1 | 0 |
| 1 | 0 | 0 |
| 1 | 1 | 1 |
| A | B | C |
|---|---|---|
| 0 | 0 | 0 |
| 0 | 1 | 1 |
| 1 | 0 | 1 |
| 1 | 1 | 1 |

MULTIDENTATE LIGAND

CROSS-REFERENCE TO RELATED APPLICATIONS

This is a continuation of Application PCT/JP03/03086, filed Mar. 14, 2003, which foreign priority benefit is based upon Japanese Application Nos. 2002-073369, 2002-179143 and 2002-288108, filed Mar. 15, 2002, Jun. 19, 2002 and Sep. 30, 2002, respectively.

BACKGROUND OF THE INVENTION

1. Field of the Invention

The present invention relates to a metal complex assembly and production thereof, which metal complex assembly is suitable for constituting nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories. The present invention also relates to a multidentate ligand that is suitable for the metal complex assembly, and to a polynuclear metal complex and a metal complex chain using the multidentate ligand.

2. Description of the Related Art

Electronic circuits using semiconductor devices serve as the backbone of technologies typically in information and communication fields and computer fields. To increase the throughput of such semiconductor devices, investigations have been made to reduce the line width of traces to be printed on a substrate and to increase a packing density of the circuit.

However, such techniques for size reduction have their limits due to quantum-theoretical influence. Thus, investigations have been made on, as a completely novel technology, molecular devices comprising a molecule or molecular assembly that works as a device.

Certain proposals have been made on driving principles and models of the molecular devices.

Batlogg et al. found that an organic crystal exhibits conductive or superconductive property by applying a technology on field-effect transistors (FET) (refer to J. H. Schon, Ch. Kolc, B. Batlogg, Nature, 406, 702 (2000)). This property is also found in fullerenes and metal complexes, is suspected to impart a switching function to various compound molecules by the action of carrier doping upon application of an electric field and receives attention.

Wada et al. proposed a model of molecular single-electron transistor comprising fullerenes as quantum dots as a candidate for single-molecular devices (refer to Japanese Patent Application Laid-Open (JP-A) No. 11-266007). According to this technology, electrodes are in tunnel junction with the quantum dot, the potential of the quantum dot is changed by the action of a voltage of a gate arranged through an insulative phase to thereby exhibit functions as a transistor.

Attempts have been made to apply a supramolecule having various structural and functional properties to switching by utilizing its molecular recognition function. The supermolecule comprises an organized assembly of plural molecules by the action of a non-covalent interaction such as coordinate bonding, hydrogen bonding and/or intermolecular force and thereby has various structural and functional properties which respective molecules alone cannot have. Balzani et al. proposed a molecular switch that changes its behavior by the action of an external field such as pH or light, using a supermolecular compound having a molecular recognition function, such as a catenane or rotaxane (refer to V. Balzani, A. Credi, and M. Venturi, Coord. Chem. Rev., 171, 3 (1998)).

Regarding wiring technologies in such molecular devices, an attempt has been made to provide wiring and connecting by introducing a functional group such as thiol group to a terminal of a conductive macromolecule and forming wiring of, for example, gold or ITO electrode utilizing chemical adsorption of the functional group with respect to the gold or ITO electrode.

As is described above, various investigations have been made on the molecular devices. However, technologies that provide practical molecular devices or circuits using the same have not yet been provided.

To design and construct the molecular device or a circuit using the same, the arrangement or array of individual molecules, recognition of individual molecules, access to individual molecules, and wiring and addressing for closely connecting between specific molecular devices to form a circuit must be carried out properly. For example, regarding the arrangement or array of individual molecules, a technique of arranging atoms one by one using a scanning probe microscope (SPM) is developing, but it is not realistic as a technique for designing or constructing nanoscale devices. Regarding the wiring, it is considered to be practical to drive the molecular devices by electron signals in a solid as in semiconductor devices. However, a macroscale conductor cannot be significantly connected to such a molecular-level device.

Molecular wires comprising a single chain macromolecule or an assembly of one-dimensionally assembled molecules may serve as an electroconductive path or a switch in the molecular devices and are believed to be a key element in the design or construction of the molecular devices or circuits using the same.

However, the electroconductive mechanisms of molecular wires are currently under study and have not yet been clarified sufficiently. In addition, such simple one-dimensional substances lose their electric conductivity due to specific properties in one-dimensional substances, such as Peierls transition, and are difficult to form into molecular wires.

Metal complex chains, especially ladder complexes are promising candidates for the molecular wire, and properties thereof have been theoretically studied initially by Rice et al. A ladder structure called as a spin ladder comprising an even number of aligned antiferromagnetic metal chains is expected to be superconductive by doping a carrier (refer to T. M. Rice, S. Gopalan and M. Sigrist, Europhys. Lett., 23 445 (1993)), and there is possibility that it functions as a device. As an experimental example, a two-leg ladder compound using a copper oxide was synthesized and was found to be superconductive under high pressure (refer to M. Uehara, T. Nagata, J. Akimitsu, H. Takahashi, H. Mori and K. Kinoshita, J. Phys. Soc. Jpn, 65, 2764 (1996)). Kimizuka et al. have investigated on the formation of the molecular wire by dispersing a halogen-bridged metal complex coated with an organic counter anion (refer to N. Kimizuka, N. Oda, T. Kunitake, Inorg. Chem. 39, 2684 (2000)). A ladder compound using a metal complex composed of p-EPYNN and Ni(dmit)$_2$ has also been studied (refer to H. Imai, T. Inabe, T. Otsuka, T. Okuno, and K. Awaga, Phis. Rev. B 54, R6838 (1996)). In addition, "crossbar switches" have been increasingly investigated as a possible candidate for a nanodevice which does not require complex processing (e.g., James R. Heath, Philip J. Kuekes, Gregory S. Snider, R. Stanley Williams, Science Vol. 280 (1998)). In the crossbar switches, the switching at the intersection point between nanowires (nanoscale wire) crossing each other is controlled by an input from the nanowires. Thus, if an array of the nanowires is constituted on the molecular level and in a bottom-up manner, ultradense devices can be relatively easily provided.

However, these are only expectations or experimental estimations and lack practicality and specificity. These cannot be significantly achieved by conventional technologies, and demands have been made on a novel technique that can realize, for example, the molecular-level wiring on the molecular level in a bottom-up manner. Certain metal complex assemblies have been synthetically prepared (refer to W. Huang, S. Gou, D. Hu, S. Chantrapromma, H. Fun, and Q.

Meng, Inorg. Chem., 40, 1712 (2001)). However, in most cases, molecules are arrayed as a ladder only by the action of a weak interaction such as intermolecular force, and it is difficult to control to pack such molecules. The molecular array of the resulting metal complex chain significantly depends on the molecular form, effects of substituents, subtle interactions between molecules and other factors and may not possibly become a ladder structure even if chemically modified. Thus, the metal complex chain cannot sufficiently serve as a single wire.

SUMMARY OF THE INVENTION

A multidentate ligand of the present invention contains at least two planar tetradentate coordination sites in one plane, each of the planar tetradentate coordination sites containing four nitrogen-containing groups selected from among at least one of imino, amido and amino groups and having the nitrogen atoms of the four nitrogen-containing groups as coordinating atoms in one plane.

A polynuclear metal complex of the present invention contains the multidentate ligand of the present invention, and central metal ions. These multidentate ligand and polynuclear metal complex each have two planar tetradentate coordination sites in one plane and can thereby be stacked. Thus, for example a metal complex chain can be constituted by stacking these as building blocks.

A metal complex chain of the present invention contains an assembly of the polynuclear metal complex of the present invention being assembled through bridging ligands. The metal complex chain structurally has assembled planes each containing the two planar tetradentate coordination sites and thereby has a ladder structure comprising the planes as a ladder. The metal complex chain can be, for example, easily assembled due to its ladder structure and is suitable for forming or constituting typically a molecular device.

The multidentate ligand, the polynuclear metal complex or the metal complex chain of the present invention can be used to constitute a metal complex assembly which is suitable for constituting nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories.

A metal complex assembly of the present invention includes metal complex chains and electroconductive wires, the metal complex chains each contain assembled metal complexes, the electroconductive wires each contains molecules serving as at least one of an acceptor and a donor, and the metal complex chains intersect with the electroconductive wires at such positions that the metal complexes and the molecules are capable of interacting with each other. Thus, an electric field applied to the electroconductive wire causes charge transfer between the metal complex chain and the electroconductive wire on the molecular level. A carrier (at least one of electron and positive hole) is doped into the metal complex chain to thereby change the electroconductivity of the metal complex chain. As a result, the electrical switching at the intersection point between the metal complex chain and the electroconductive wire can be externally controlled on the molecular level.

The metal complex assembly of the present invention has one of a two-dimensional and three-dimensional structures and generally has a single-crystal or thin-film structure, in which the electroconductive wires extend and reach the edges of the single crystal or thin film. Thus, when a voltage is externally applied to the electroconductive wire in the metal complex assembly, the amount of the carrier (at least one of electron and positive hole) doped into the metal complex chain can be controlled. The metal complex assembly therefore permits switching of a current on the molecular level. The metal complex assembly is suitable for nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories.

A method of the present invention produces a metal complex assembly by subjecting polynuclear metal complexes and pi-conjugated planar molecules to electrolysis reaction, the polynuclear metal complexes being to coordinate with a halogen ion as a bridging ligand, and the pi-conjugated planar molecules each being halogenated at two or more positions. Thus, the polynuclear metal complexes include the halogen ions as a bridging ligand to form a one-dimensional chain. The pi-conjugated planar molecules undergo electrochemical polymerization catalyzed by the polynuclear metal complexes. As a result, the one-dimensional chain composed of the polynuclear metal complexes and the electroconductive wire composed of pi-conjugated planar molecules are simultaneously precipitated and formed.

BRIEF DESCRIPTION OF THE DRAWINGS

FIG. 2A is a schematic view of an example of a nickel(III) (represented by M) complex chain which is a metal complex chain of a ladder structure comprising nickel complexes being assembled through a halogen (X) as a bridging ligand. FIG. 2B is an example of a structural formula of a ligand constituting a metal complex chain of a spin-ladder structure.

FIG. 10A is a schematic view illustrating the operation of an AND circuit in which output C is done only in the case where both Input A and Input B are done.

FIG. 10B is a schematic view illustrating the operation of an OR circuit in which an output C is done in the case where Input A, or Input B or both are done.

DESCRIPTION OF THE PREFERRED EMBODIMENTS

Figure 1A:
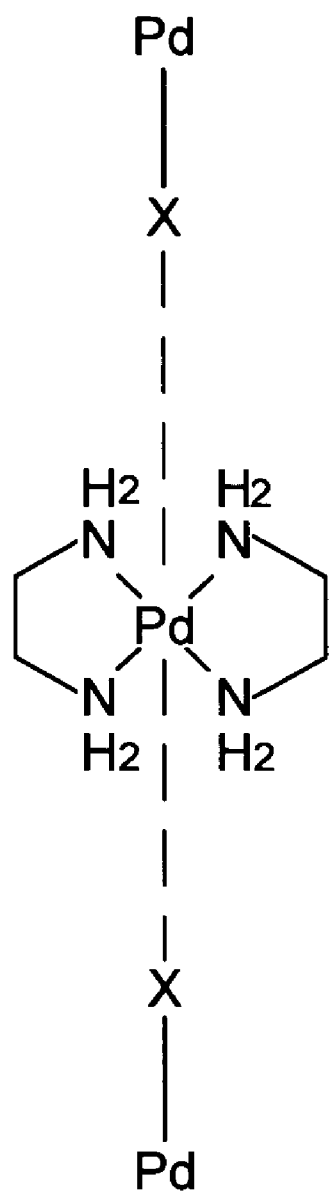
FIG. 1A is a schematic view of an example of a metal complex chain comprising assembled metal complexes, in which the metal complexes each comprise ethylenediamine as a ligand and palladium as a central metal ion and are assembled through a halogen (X) as a bridging ligand.

An object of a present invention is to solve the problems in conventional technologies, to meet the demands and to provide a metal complex assembly which is suitable for constituting nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories. Another object of a present invention is to provide a method for efficiently producing the metal complex assembly. Yet another object of a present invention is to provide a multidentate ligand that is suitable for the metal complex assembly, a polynuclear metal complex and a metal complex chain using the multidentate ligand.

Multidentate Ligand

The multidentate ligand of the present invention comprises at least two planar tetradentate coordination sites in one plane and may further comprise, for example, substituents according to necessity.

Each of the planar tetradentate coordination sites comprises four nitrogen-containing groups, in which the nitrogen atoms in the four nitrogen-containing groups are each arranged in one plane as coordinating atoms. Namely, the four nitrogen atoms arranged in one plane in the planar tetradentate coordination site.

The nitrogen-containing group can be any group that contains at least one nitrogen atom and can be suitably selected according to the purpose. The nitrogen-containing groups are preferably at least one of imine, amido and amino groups. The four nitrogen-containing groups may be the same as or different from one another.

The planar tetradentate coordination sites may further have, for example, substituents as long as not adversely affecting the advantages of the present invention.

The multidentate ligand of the present invention can constitute, in combination with central metal ions, the polynuclear metal complex of the present invention. The polynuclear metal complex can constitute the metal complex chain of the present invention by stacking the same as a building block and can further constitute the metal complex assembly of the present invention. The multidentate ligand of the present invention is suitable for constituting nanoscale devices capable of operating at ultrahigh density and ultrahigh speed, such as molecular devices, matrix circuits, molecular functional devices and logical circuits, is useful for devices and apparatuses in information and communication fields, such as arithmetic and logic units, displays and memories and is advantageously applicable to the miniaturization and elaboration such devices and apparatuses.

The multidentate ligand preferably has a structure in which two of the planar tetradentate coordination sites are adjacent to each other. More preferably the multidentate ligand has a structure that is capable of structurally or electrically connecting between two central metal ions by the action of a pi-conjugated system when the ligand constitutes a polynuclear metal complex in which the two central metal ions are arranged respectively in two planar tetradentate coordination sites.

When the multidentate ligand has such a structure, planar dopant molecules can be sandwiched by stacked layers to thereby form a metal complex assembly that can more efficiently transfer charges through a pi-pi interaction.

The multidentate ligand specifically preferably has two of the planar tetradentate coordination sites in one plane through an aromatic ring.

This configuration is advantageous in that, when the metal complex chain is formed, the two central metal ions can be coupled through a pi-conjugated system.

The aromatic ring is not specifically limited, can be suitably selected according to the purpose, and preferred examples thereof are benzene ring, pyrazine ring, and derivatives thereof. These can be substituted with one or more substituents. The aromatic ring is more preferably one of benzene ring and pyrazine ring.

The specific structure of the multidentate ligand is not specifically limited and can be suitably selected according to the purpose. In preferred embodiments thereof, nitrogen atoms in two of the four nitrogen-containing groups are each bound to the aromatic ring.

Specific examples of such preferred embodiments are (A) a first embodiment in which the four nitrogen-containing groups are combined to form a macrocycle (first embodiment in which the planar tetradentate coordination site is formed in the macrocycle), (B) a second embodiment in which each of nitrogen atoms in two of the four nitrogen-containing groups is directly bound to the aromatic ring and indirectly bound to a cyclic structure, and each of nitrogen atoms in the other two is directly bound to the cyclic structure, (C) a third embodiment in which each of nitrogen atoms in two of the four nitrogen-containing groups is a nitrogen constituting a nitrogen-containing ring, and each of nitrogen atoms in the other two is directly bound to the aromatic ring and indirectly bound to the nitrogen-containing ring, and (D) a fourth embodiment in which each of nitrogen atoms in two of the four nitrogen-containing groups is a nitrogen constituting an amide or imine directly bound to the aromatic ring, and each of nitrogen atoms in the other two is directly bound to a carbon chain having the amide or imine at one end.

The multidentate ligands according to these embodiments can constitute a metal complex assembly which is suitable for constituting nanoscale devices capable of operating at ultra-high density and ultrahigh speed, such as molecular devices, matrix circuits, molecular functional devices and logical circuits and is applicable to the miniaturization and elaboration of devices and apparatus in information and communication fields, such as arithmetic and logic units, displays and memories.

Of the first embodiment, multidentate ligands represented by at least one of following Formulae (1), (2), (3), (4), (9), (11), (12) and (14) are typically preferred.

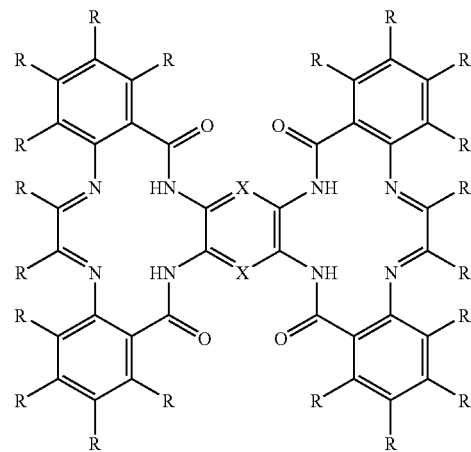

Formula (2)

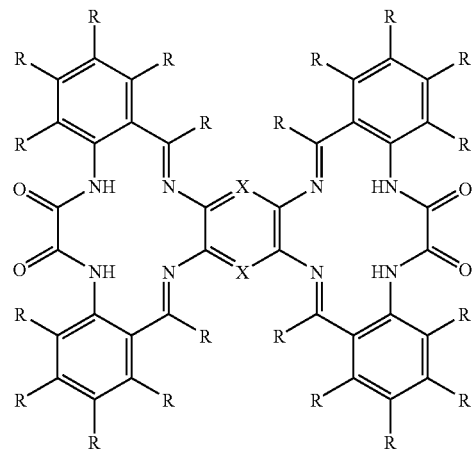

Formula (3)

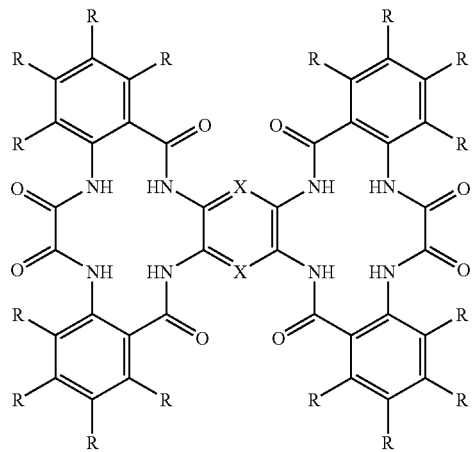

Formula (1)

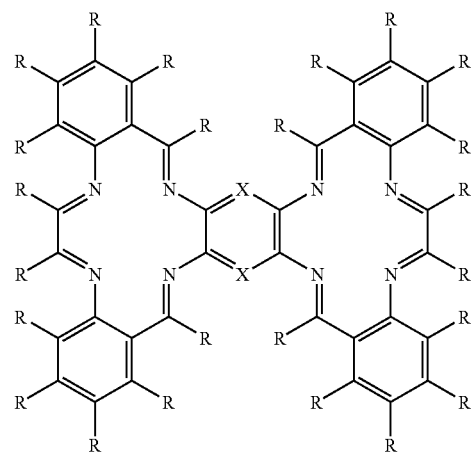

Formula (4)

Formula (9)
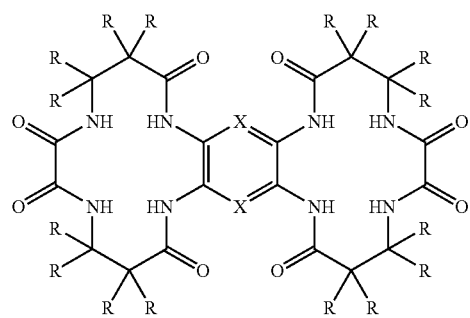
Formula (11)
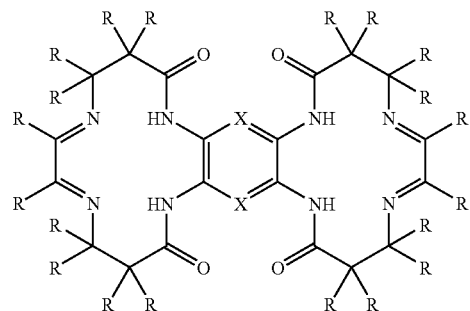
Formula (12)
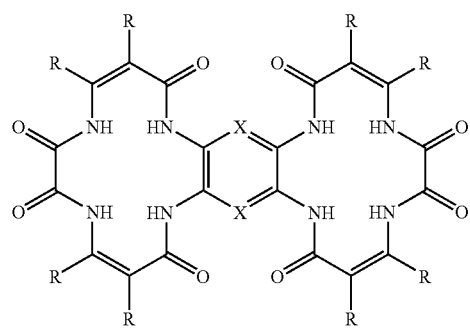
Formula (14)
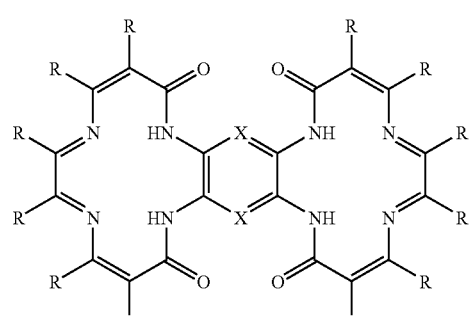
Of the second embodiment, multidentate ligands represented by at least one of following Formulae (5) and (6) are typically preferred.
Formula (5)
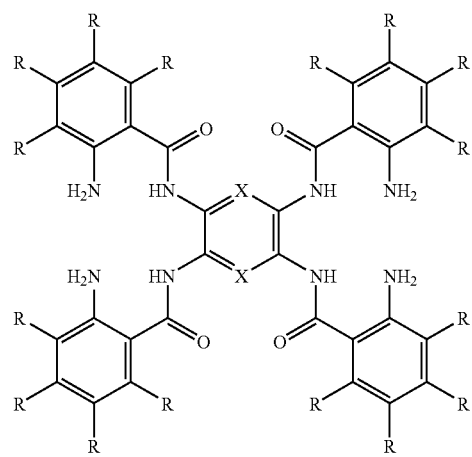
Formula (6)
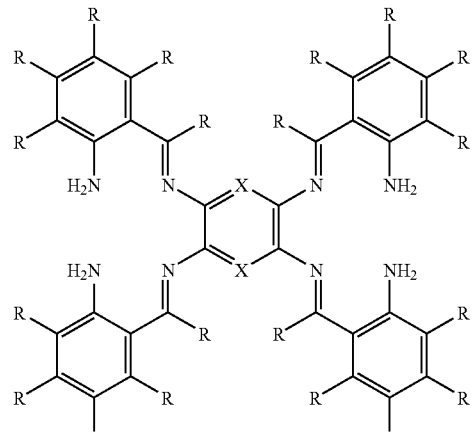
Of the third embodiment, multidentate ligands represented by at least one of following Formulae (7) and (8) are typically preferred.
Formula (7)
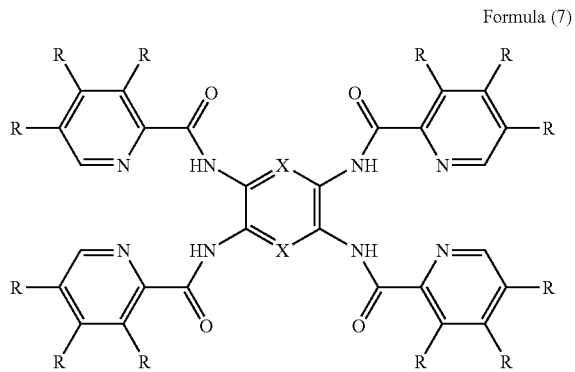

Formula (8)

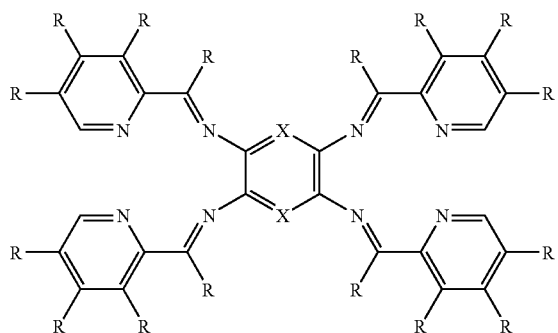

Of the fourth embodiment, multidentate ligands represented by at least one of following Formulae (10) and (13) are typically preferred.

Formula (10)

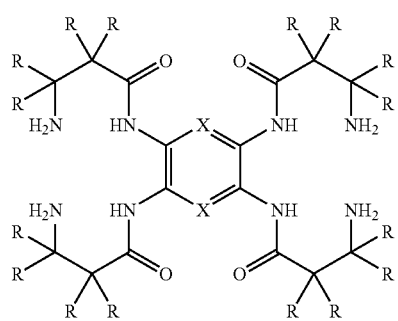

Formula (13)

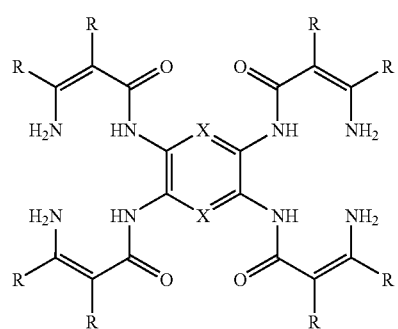

In Formulae (1) through (14), Rs are the same as or different from each other and are each hydrogen atom or a substituent; and X is at least one of carbon and nitrogen or a group containing at least one of carbon and nitrogen.

The substituent represented by R is not specifically limited, can be suitably selected according to the purpose and is preferably at least one of alkyl groups, alkoxy groups, aryloxy groups, hydroxyl group, thiol group, amino group, and halogen atoms.

Examples of the alkyl groups are methyl group, ethyl group, propyl group and butyl group.

Examples of the alkoxy groups are methoxy group, ethoxy group, propoxy group and butoxy group.

Examples of the halogen atoms are fluorine, chlorine, bromine and iodine atoms.

Among these substituents, hydroxyl group and thiol group are typically preferred for satisfactorily controlling interactions between chains.

The multidentate ligand of the present invention can be synthetically prepared according to a suitable procedure such as electrolytic synthesis.

The multidentate ligand of the present invention can be suitably used in various fields and is useful, for example, in the polynuclear metal complex, the metal complex chain and the metal complex assembly of the present invention mentioned below.

(Polynuclear Metal Complex)

The polynuclear metal complex of the present invention comprises the multidentate ligand of the present invention and central metal ions and may further comprise other components according to necessity.

The multidentate ligand herein is identical to the multidentate ligand of the present invention.

The central metal ions are not specifically limited and can be suitably selected according to the purpose. They are preferably transition metal ions which will form a hexadentate structure in the metal complex chain (a planar tetradentate structure before included in the metal complex chain). By incorporating such transition metal ions as the central metal ions, the resulting metal complex chain tends to form a stable ladder structure.

Among these transition metal ions, the central metal ions are preferably at least one of ions of Ni(II), Ni(III), Cu(II), Zn(II), Co(II), Cr(II), Mn(II), Fe(II), Pd(II), Pt(II), Ru(II), Rh(II), Ag(II), and Au(III). Thus, the metal complex chain can constitute a metal complex assembly having a ladder structure of strongly correlated electron system. This type of metal complex assembly is suitable for constituting nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories.

The central metal ions are respectively coordinated to the two planar tetradentate coordination sites in the multidentate ligand.

Namely, two central metal ions are coordinated to one multidentate ligand. The two central metal ions may be the same as or different from each other.

The polynuclear metal complex preferably has a structure in which two of the planar tetradentate coordination sites in the multidentate ligand are adjacent to each other. The two central metal ions coordinated to the multidentate ligand are structurally or electrically coupled with each other preferably by the action of a pi-conjugated system and more preferably through an aromatic ring.

Thus, planar dopant molecules can be arranged between layers upon stacking to form a metal complex assembly. The resulting metal complex assembly can more efficiently transfer charges through pi-pi interactions.

The aromatic ring is not specifically limited, can be suitably selected according to the purpose and is, for example, benzene ring, pyrazine ring, and derivatives thereof. These may be substituted with one or more substituents. Among these, at least one of benzene ring and pyrazine ring is preferred as the aromatic ring.

The polynuclear metal complex of the present invention can be synthetically prepared according to a suitable procedure such as electrolytic synthesis.

The polynuclear metal complex of the present invention can be suitably used in various fields and is advantageously used in the metal complex chain and the metal complex assembly according to the present invention mentioned below.

(Metal Complex Chain)

The metal complex chain of the present invention comprises an assembly of the polynuclear metal complexes of the present invention through bridging ligands.

The metal complex chain has a ladder structure as an intermediate state between a one-dimensional chain and a two-dimensional chain. As is described above, a metal complex chain of a spin-ladder structure comprising an even number of aligned antiferromagnetic metal chains may possibly exhibit superconductivity by carrier doping. It has been experimentally confirmed that a metal complex chain having a two-leg ladder structure and comprising a copper oxide becomes superconductive under high pressure.

The bridging ligands are not specifically limited, can be suitably selected according to the purpose and are preferably at least one of halogen ions, pyrazine, bipyridine and analogous compounds thereto. Thus, by using this type of bridging ligand in combination with a polynuclear metal complex of a metal of strongly correlated electron system as the polynuclear metal complex, the resulting metal complex chain or the metal complex assembly using the same can exhibit not only a switching function with respect to metallic conductivity but also superconductive transition capability due to the interaction between the bridging ligand and the metal of strongly correlated electron system.

Among the metal complex chains, preferred are metal complex chains in which the central metal ions of the multidentate ligand in the polynuclear metal complex each have an unpaired electron, and the spins of the unpaired electrons are arranged in anti-parallel through the bridging ligand, i.e., metal complex chains having a spin ladder structure. These metal complex chains are expected to exhibit satisfactory electroconductivity or superconductivity. Among them, those having properties of strongly correlated electron system are more preferred.

For satisfactory electroconductivity or superconductivity, the metal complex chain preferably has a structure in which pi-conjugated planar molecules serving as at least one of an acceptor and a donor are positioned between layers of the assembled polynuclear metal complexes. For further improved electroconductivity, the metal complex chain has an alternating stacked structure comprising the polynuclear metal complexes and the pi-conjugated planar molecules being arrayed in physically alternate order and has a separated and stacked structure in which the metal complex chain and pi-electron column are electrically arranged in parallel, which metal complex chain comprising the stacked polynuclear metal complexes and the pi-conjugated planar molecules.

In the case where the multidentate ligands in the polynuclear metal complexes are represented by at least one of Formulae (1), (2), (5), (7), (9), (10), (11), (12), (13) and (14), carbonyl group in the vicinity of the aromatic ring in the multidentate ligands is preferably capable of interacting with the pi-conjugated planar molecules serving as at least one of an acceptor and a donor.

In the case where the multidentate ligands in the polynuclear metal complexes are represented by at least one of Formulae (3), (4), (6) and (8), the substituent R in the vicinity of the aromatic ring in the multidentate ligands is preferably capable of interacting with the pi-conjugated planar molecules serving as at least one of an acceptor and a donor.

The metal complex chain of the present invention can be synthetically prepared according to a suitable procedure such as electrolytic synthesis.

The metal complex chain of the present invention can be suitably used in various fields and is advantageously used in the metal complex assembly of the present invention mentioned below.

(Metal-Complex Assembled Structure and Production Method Thereof)

The metal complex assembly of the present invention comprises metal complex chains and electroconductive wires intersecting with each other and has one of a two-dimensional structure and three-dimensional structure.

The electroconductive wires comprise molecules serving as at least one of an acceptor and a donor, and the electroconductive wires intersect with the metal complex chains at such positions that the metal complexes in the metal complex chains are capable of interacting with the molecules serving as at least one of an acceptor and a donor.

-Metal Complex Chain-

The constitutive metal complex chain is not specifically limited and can be suitably selected according to the purpose as long as it comprises an assembly of metal complexes. The metal complex chain has received attention as a material for molecular wires other than inorganic compounds such as copper oxide, as described above.

The constitutive metal complex comprises a central metal ion and a ligand and may further comprise one or more other components according to necessity.

When the ligand is an organic compound, the metal complex is an inorganic-organic compound complex and can control its structure and physical properties. A one-dimensional metal complex comprising the central metal ions being regularly arrayed through, for example, a ligand can be specifically advantageously used as an electroconductive molecular wire.

The central metal ion is not specifically limited and can be suitably selected according to the purpose. It is preferably a metal ion which forms a hexadentate structure in the metal complex chain (a planar tetradentate structure before included in the metal complex chain), such as Ni(II), Ni(III), Cu(II), Zn(II), Co(II), Cr(II), Mn(II), Fe(II), Pd(II), Pt(II), Ru(II), Rh(II), Ag(II), and Au(III) ions. By incorporating such a metal ion as the central metal ion, the resulting metal complex chain tends to form a stable one-dimensional structure or ladder structure. Among them, ions of nickel and copper (Ni(III), Cu(II)) which are strongly correlated electron system metals are more preferred.

When the strongly correlated electron system metal is used as the central metal ion, the ligand is preferably selected from, for example, a halogen, pyrazine and bipyridine to constitute an assembly of the metal complexes to thereby constitute the metal complex chain. By using the ligand of this type, the resulting metal complex chain or the metal complex assembly using the same can exhibit not only a switching function to metallic conductivity but also superconductive transition capability. These properties are induced by the interaction between the bridging ligand and the metal of strongly correlated electron system.

The metal complex chain or the metal complex assembly exhibiting superconductive transition capability can work to produce, for example, fine molecular devices, matrix circuits, molecular functional devices and logical circuits that avoid heat production problems. Especially, it is advantageous to constitute nanoscale devices in which the circuit is very fine and is difficult to radiate heat.

Regarding the superconductive transition capability, certain high-temperature superconducting oxides have been known. In these high-temperature superconducting oxides, superconducting phenomenon occurs by doping a carrier to a substance having strong electron correlation, namely a Mott insulator (Mott insulator in a strongly correlated electron system). Halogen-bridged nickel(III) complexes have been reported as substances that become Mott insulators in a strongly correlated electron system (H. Okamoto, Y. Shimada, Y. Oka, A. Chainani, T. Takahashi, H. Kitagawa, T. Mitani, K. Toriumi, K. Inoue, T. Manabe and M. Yamashita, Phys. Rev., B54, 8438 (1996)).

The ligand is not specifically limited, can be suitably selected according to the purpose and is preferably one having a structure that can constitute a planar metal complex. Examples of such ligands are ethylenediamine, cyclohexanediamine and glyoxime. Each of these ligands can be used alone or in combination. However, the ligands are preferably selected so as to have a regular array.

The ligand may be preferably substituted with, for example, hydroxyl group and/or carboxyl group. Thus, the ligands in adjacent metal complex chains can interact with each other due to, for example, hydrogen bonding. Consequently, an electroconductive path (electroconductive molecular wire) is formed between the adjacent metal complex chains to thereby form a metal complex assembly having a three-dimensional structure.

Among the ligands, the multidentate ligands of the present invention are preferred. By using the multidentate ligand of the present invention, the resulting metal complex assembly is suitable for constituting nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories.

The metal complex chain is not specifically limited and can be suitably selected according to the purpose, as long as it comprises a structural assembly of the metal complexes. It is preferably one of one-dimensional chains and the metal complex chains of the present invention for typically constituting nanoscale fine molecular devices, matrix circuits of three-dimensional network structure, molecular functional devices and logical circuits. The metal complex chains of the present invention are more preferred as the metal complex chain for exhibiting the superconductive transition capability and effectively avoiding heat production problems, of which the spin-ladder chain is further preferred.

Examples of the one-dimensional chains are metal complex chains comprising an assembly of metal complexes having a ligand that can form a planar metal complex.

Figure 1B:
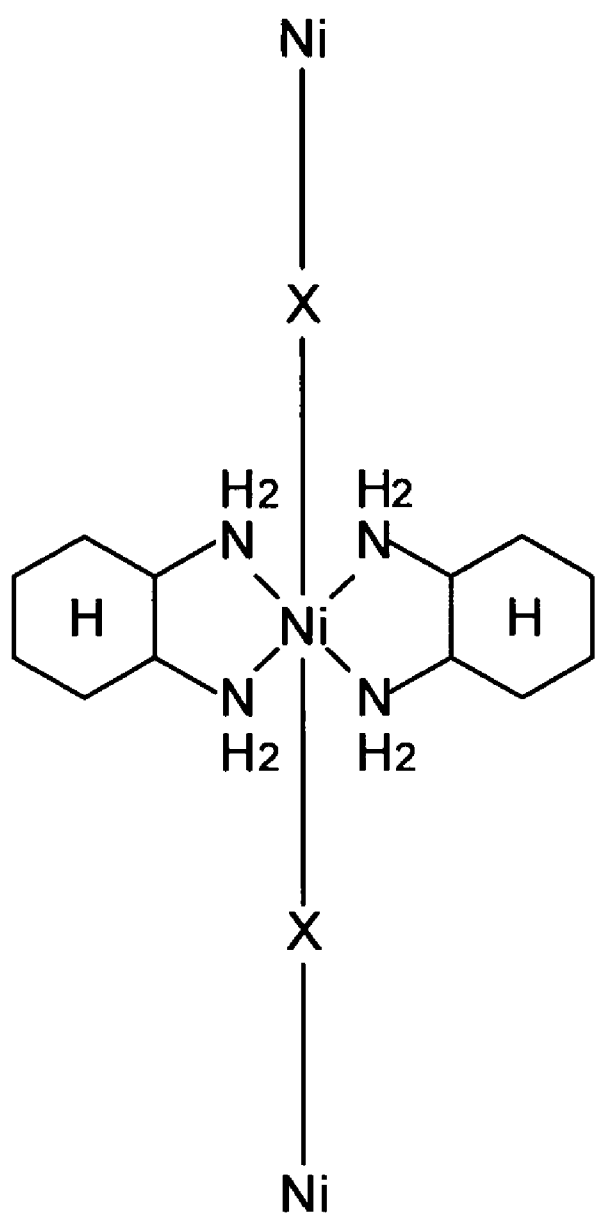
FIG. 1B is a schematic view of another example of a metal complex chain comprising assembled metal complexes, in which the metal complexes each comprise cyclohexanediamine as a ligand and nickel as a central metal ion and are assembled through a halogen (X) as a bridging ligand.

Examples of the one-dimensional chains are metal complex chains each comprising an assembly of metal complexes with bridging ligands in alternate order, in which the metal complexes each comprise a ligand such as ethylenediamine, cyclohexanediamine or glyoxime and a central metal ion as shown in FIGS. 1A and 1B. Specific examples thereof are metal complex chains each comprising at least one of a halogen-bridged bis(cyclohexanediaminato)nickel complex and a halogen-bridged bis(ethylenediaminato)palladium complex.

As is described above, the metal complex chain of the present invention has a ladder structure. Among such ladder structures, the spin-ladder chain is preferred in the present invention. The spin-ladder chain is not specifically limited, can be suitably selected according to the purpose, and preferred examples thereof are a metal complex chain (FIG. 2A) comprising an assembly of metal complexes each containing a ligand having the structure shown in FIG. 2B, and a metal complex chain using the polynuclear metal complex of the present invention.

These metal complexes contain a pi-conjugated system, have a planar structure and can thereby easily constitute a stacked structure in which the molecules serving as at least one of an acceptor and a donor and having a pi-conjugated system are arranged between its layers. The resulting metal complex chain comprising an assembly of the metal complexes can work to effectively transfer electrons through pi-electron cloud.

Rice et al. reported that the metal complex chain having a spin-ladder structure (hereinafter may be briefly referred to as "spin-ladder chain") has a structure of an intermediate state between a one-dimensional chain and a two-dimensional chain, exhibits an antiferromagnetic interaction caused by the superexchange interaction of the bridging ligands in at least one of the extending direction of the metal complex chain (assembling direction of the metal complexes) and the interlayer direction of the metal complex chain (a direction substantially perpendicular to the assembling direction), and that the metal complex chain may exhibit electroconductivity or superconductivity by carrier doping. They also indicated that, in the case of the spin-ladder chain, spin pairs may be formed only in the ladder system to thereby exhibit a superconducting state, in contrast to systems with interactions of pure one-dimensional chain, two-dimensional chain or three-dimensional chain. Thus, the use of the spin-ladder chain as the metal complex chain can yield a metal complex assembly which is suitable, for example, for fine molecular devices, matrix circuits, molecular functional devices and logical circuits which avoid heat production problems.

The constitutive electroconductive wires are not specifically limited, can be suitably selected according to the purpose, as long as they comprise a molecule serving as at least one of an acceptor and a donor, and preferred examples thereof are those in which a plurality of the compound serving as at least one of an acceptor and a donor are coupled with each other so as to transfer electrons. Each of these can be used alone or in combination.

The compounds can be coupled by any suitable means, such as covalent bonding or hydrogen bonding.

Figure 3:
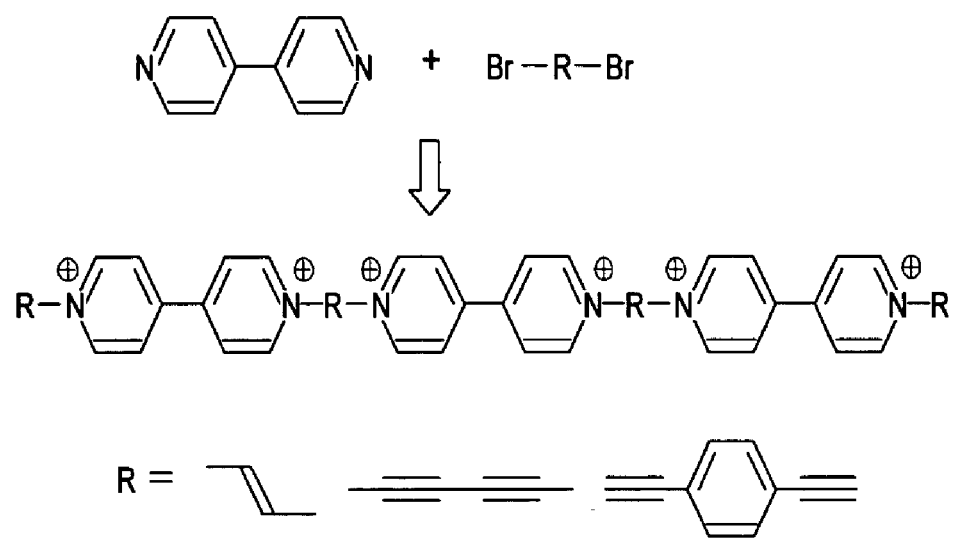
FIG. 3 is an example of an electroconductive wire prepared as a result of the reaction of 4,4'-bipyridyl and dibromoalkyl, and an example of a structural formula of an electroconductive polymer prepared by polymerizing p-dibromobenzene or 4,4'-dibromobiphenyl.
Figure 3:
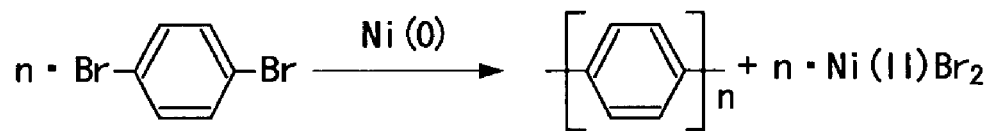
Figure 3:
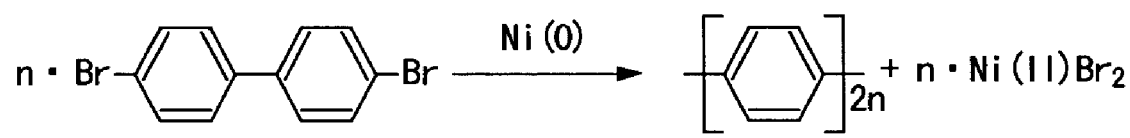

Specific examples of the electroconductive wires are an electroconductive wire prepared by reacting 4,4'-bipyridyl and a dibromoalkyl, and an electroconductive wire composed of a poly-p-phenylene prepared by polymerizing p-dibromobenzene or 4-4'-dibromobiphenyl, as shown in FIG. 3. In FIG. 3, the arrows each represent the direction of the reaction; and "Ni(O)" represents a nickel complex.

The electroconductive wires intersect with the metal complex chains at such positions that the molecules serving as at least one of an acceptor and a donor can interact with the metal complexes in the metal complex chain.

The interaction may be, for example, at least one of donation and acceptance of a carrier (at least one of electron and positive hole). The interaction can be one or more types of interactions.

The angle of intersection is not specifically limited, can be suitably set according to the purpose and is preferably about 90 degrees for constituting a three-dimensional network.

When an electric field is applied to the electroconductive wire in the metal complex assembly of the present invention, charge transfer on the molecular level occurs between the metal complex chain and the electroconductive wire. As a result, a carrier (at least one of electron and positive hole) is doped into the metal complex chain (carrier doping). Thus, the electroconductivity of the metal complex chain are changed from insulative properties to metallic properties or superconductive properties as a result of carrier doping, when the metal complex in the metal complex chain is a substance exhibiting a strong electron correlation, such as a nickel complex or copper complex.

The metal complex assembly has a two-dimensional or three-dimensional structure in which the electroconductive wires intersect with the metal complex chains, and the electroconductive wires extend and reach the edges of the single crystal or thin film. The amount of the carrier (at least one of electron and positive hole) passing through the metal complex chain can be controlled when a voltage is externally applied to the electroconductive wire in the metal complex assembly. Thus, the metal complex assembly can realize switching of a current on the molecular level. The metal complex assembly is suitable for constituting nanoscale devices capable of operating at ultrahigh density and ultrahigh speed, such as molecular devices, matrix circuits, molecular functional devices and logical circuits and is applicable to the miniaturization and elaboration of devices and apparatus in information and communication fields, such as arithmetic and logic units, displays and memories.

Figure 4:
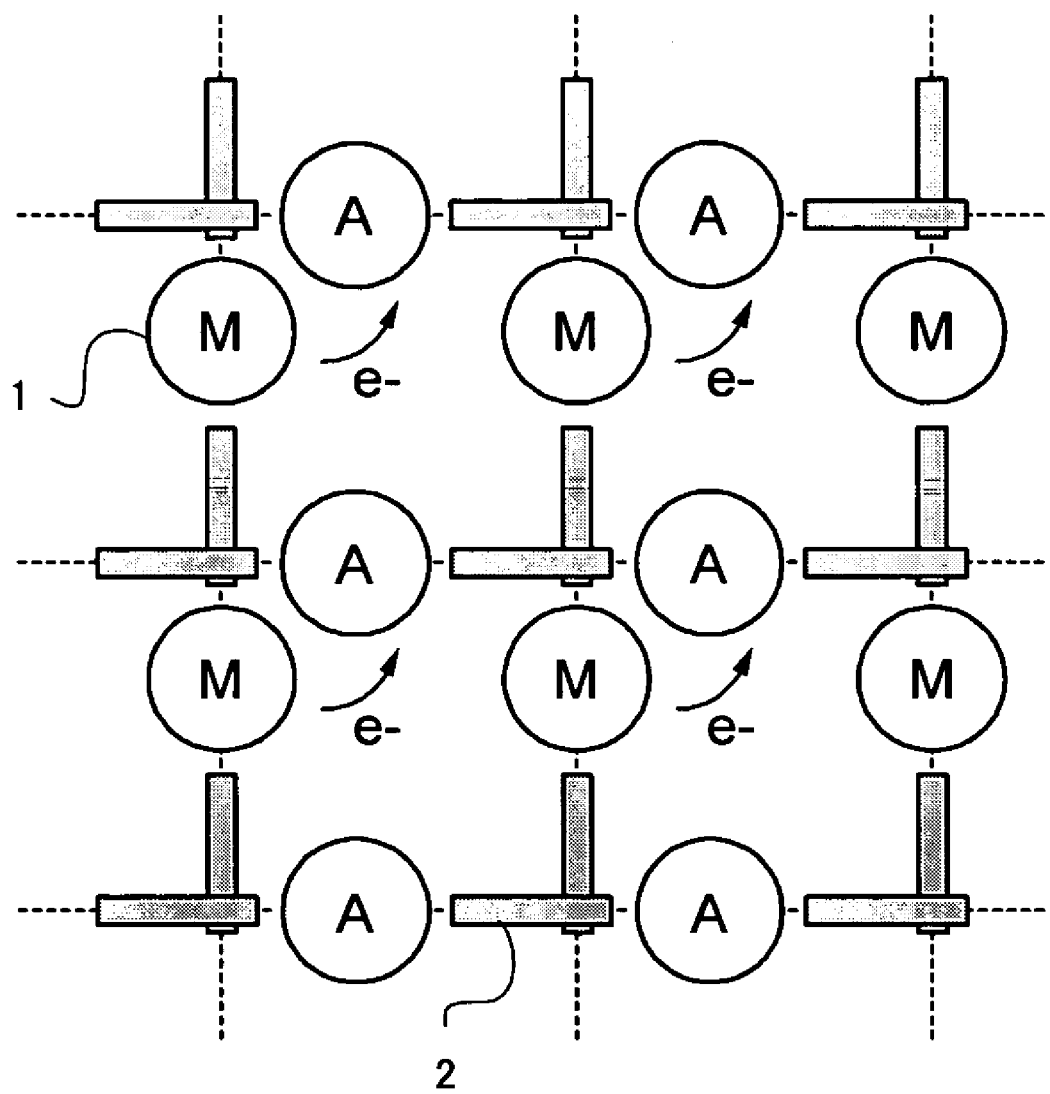
FIG. 4 is an explanatory schematic view of an example of a two-dimensional structure in the metal complex assembly.
Figure 5:
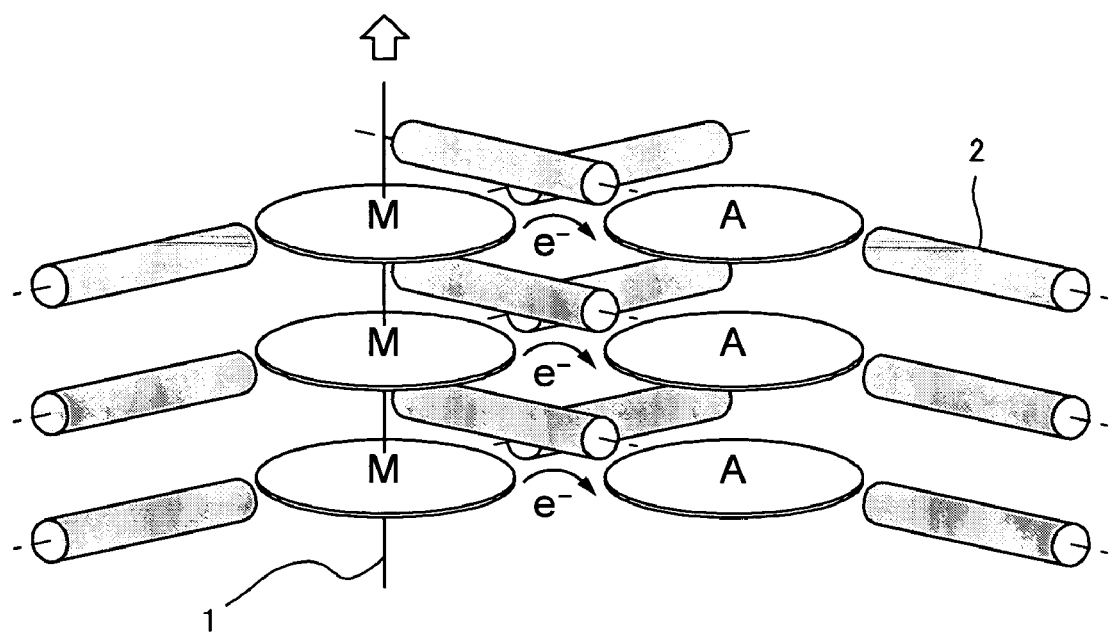
FIG. 5 is an explanatory schematic view of an example of a three-dimensional structure in the metal complex assembly.

FIGS. 4 and 5 are explanatory schematic views of an example of the configuration of the metal complex assembly. In the example shown in FIGS. 4 and 5, the metal complex assembly comprises metal complex chains 1 and electroconductive wires 2. The metal complex chains 1 each comprise an assembly of the metal complexes. The electroconductive wires 2 each comprise the molecule serving as at least one of an acceptor and a donor. The metal complex chains 1 intersect with the electroconductive wires 2 at such positions that the metal complexes and the molecules serving as at least one of an acceptor and a donor can interact with (transfer charges to) each other. Thus, by applying a voltage to the electroconductive wire 2, charge transfer occurs between the metal complex chain 1 and the electroconductive wire 2 in the example shown in FIGS. 4 and 5. The charge transfer causes charge doping into the metal complex chain 1, and a current in the assembling direction of the metal complex chain 1 (extending direction of the metal complex chain) can be switched to turn ON or OFF. The symbol "e$^-$" represents an electron and the arrow attached to "e$^-$" represents the direction of movement of the electron in FIGS. 4 and 5. The arrow in FIG. 5 represents the direction of electrical conduction.

Figure 11:
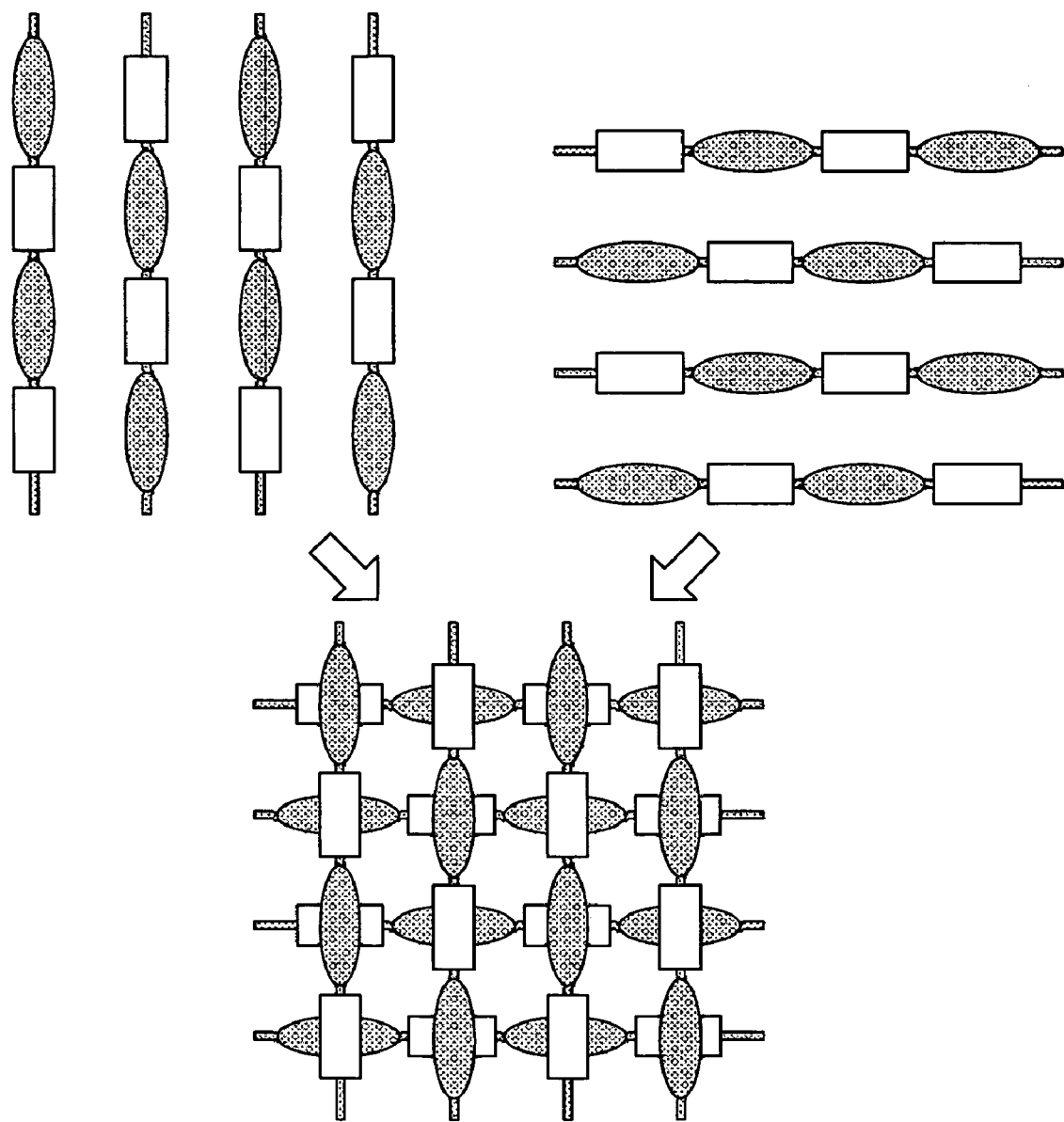
FIG. 11 is a schematic plan view of an example of a metal complex assembly having a stacked layer structure. Each of the layers comprises one-dimensional chains containing molecules serving as at least one of an acceptor and a donor and metal complexes combined in alternate order. The one-dimensional chains are arrayed two-dimensionally so that the molecules and the metal complexes are adjacent to each other. In this structure, the layers are stacked so that the molecules and the metal complexes are adjacent to each other and the one-dimensional chains in adjacent layers intersect at right angles.
Figure 12:
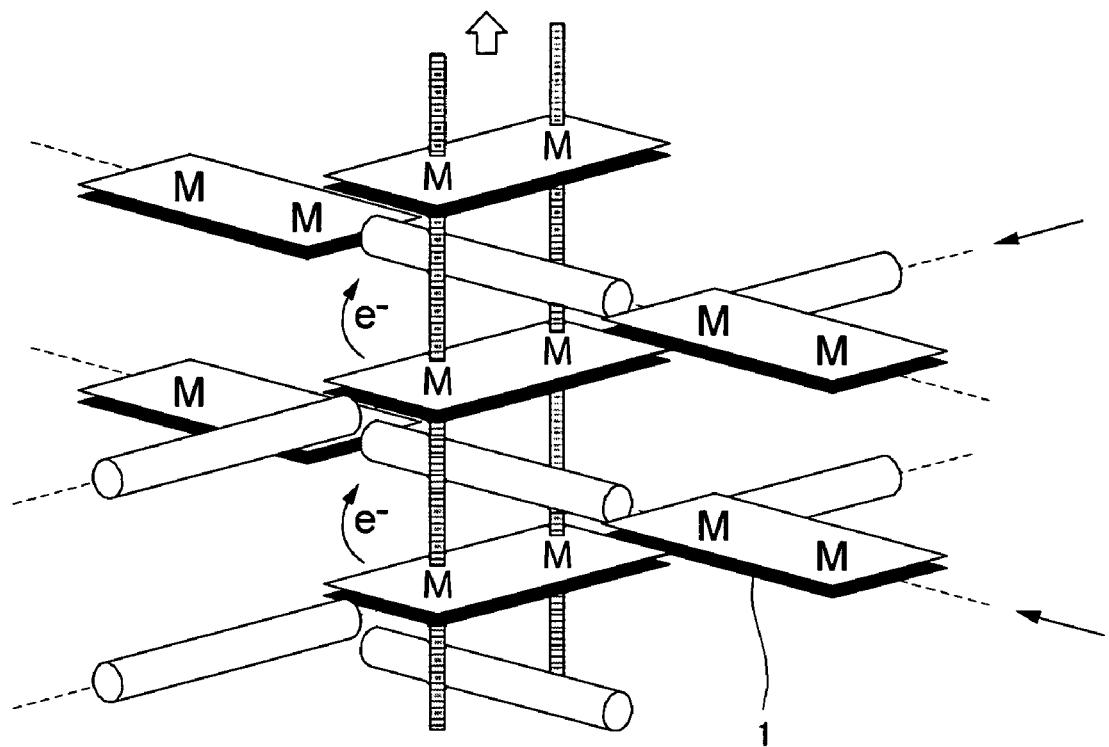
FIG. 12 is a schematic perspective view of an example of the metal complex assembly shown in FIG. 11, in which the molecules serving as at least one of an acceptor and a donor penetrate the polynuclear metal complexes at intersection points between the one-dimensional chains.

FIGS. 11 and 12 are explanatory schematic views of an example of the configuration of the metal complex assembly. In FIG. 11, the symbol "open square" represents a polynuclear metal complex; and the ellipse represents a molecule serving as an acceptor or a molecule serving as a donor. In FIG. 12, the symbol "e$^-$" represents an electron; the arrow attached to "e$^-$" represents the direction of movement of the electron; the up-pointing arrow represents the direction of electrical conduction; the rectangle including "M" represents the polynuclear metal complex; the cylinder represents a molecule serving as an acceptor or a molecule serving as a donor; the symbol "→" represents the direction of applied electric field. In the metal complex assembly shown in FIG. 11, the polynuclear metal complexes and the molecules serving as at least one of an acceptor and a donor are coupled through an interaction such as hydrogen bonding to form a one-dimensional chain in the same one plane as the coordination plane. A plurality of the one-dimensional chain is stacked so that the central metal ions in the one-dimensional chains are arranged transversely through the bridging ligand, and a ladder metal complex chain is formed in a direction perpendicular to the one-dimensional chain. With reference to FIG. 12, the metal complex assembly constitutes a three-dimensional network, in which the one-dimensional chains penetrate into between polynuclear metal complexes 1 having the ladder structure, and the molecular wires are self-aligned three-dimensionally and orthogonally. More specifically, one-dimensional chains comprising the polynuclear metal complexes coupled with the molecules serving as at least one of an acceptor and a donor through hydrogen bonding are arrayed orthogonally to each other. The molecules serving as at least one of an acceptor and a donor in the one-dimensional chain penetrate through a center portion of the polynuclear metal complex in the one-dimensional chain. In addition, the molecules serving as at least one of an acceptor and a donor in the one-dimensional chain undergo pi-pi stacking with a part of the polynuclear metal complexes.

When the polynulcear complex is used in combination with the molecule exhibiting acceptability, the charge transfer is accelerated to introduce positive holes as the carrier, the electric conduction switch of the ladder complex chain works, and the circuit is ON in the case where the molecule serving as an acceptor is positioned at the intersection point of an address line to which a positive potential is applied and the polynuclear metal complex resides at the intersection of an address line to which a negative potential is applied. In contrast, the charge transfer is inhibited, the switch does not work and the circuit is OFF when the molecule serving as an acceptor is positioned at the intersection point of an address line to which a negative potential is applied.

In the metal complex assembly, the molecular wires orthogonally intersecting with each other are one-dimensional chains of the identical type. Thus, single crystal (three-dimensional structure) has more isotropic symmetry, can be more easily assembled, is more stable and has more identical aspect ratio than one comprising one-dimensional chains of different types. In adjacent one-dimensional chains each comprising the polynuclear nickel complexes and the molecules in alternate order, the polynuclear nickel complex in one of the adjacent one-dimensional chains faces the molecule in the other. Thus, the polarity of the potential to apply to the address lines is opposite between the adjacent one-dimensional chains. The metal complex assembly can avoid leakage of input signals to adjacent lines, thereby avoid misoperation and can be specifically advantageously applied to, for example, arithmetic and logic units, displays and memories. Such leakage and resulting misoperation are concerns in conventional fine circuits.

The metal complex assembly of the present invention is suitably applicable typically to nanoscale molecular devices, matrix circuits, molecular functional devices, and logical circuits as mentioned below.

<Molecular Device>

The metal complex assembly of the present invention has the above-mentioned structure and functions and is applicable to a molecular device. In this case, the molecular device has a single-crystal or thin-film structure in which the metal complex chains intersect with the electroconductive wires, and the electroconductive wires extend and reach edges of the single crystal or thin film. When a voltage is applied to the electroconductive wire to transfer signals, a charge transfers from the electroconductive wire to the metal complex chain. Thus, the concentration of the carrier injected into the metal complex chain can be controlled from outside of the single crystal or thin film, and the electroconductivity of the metal complex chain in its assembling direction can be suitably controlled. Consequently, molecular devices that are free from wiring problems and have the function as a fine switching device on the molecular level can be designed.

<Matrix Circuit>

The metal complex assembly of the present invention has the above-mentioned structure and functions and is applicable to a matrix circuit. In this case, the resulting matrix circuit has a three-dimensional network structure by introducing an interaction such as chemical bonding into between adjacent metal complex chains to form an electroconductive path.

The electroconductive path can be formed by the interaction between the adjacent metal complex chains. The interaction is not specifically limited, can be suitably selected according to the purpose and is preferably hydrogen bonding.

Figure 6:
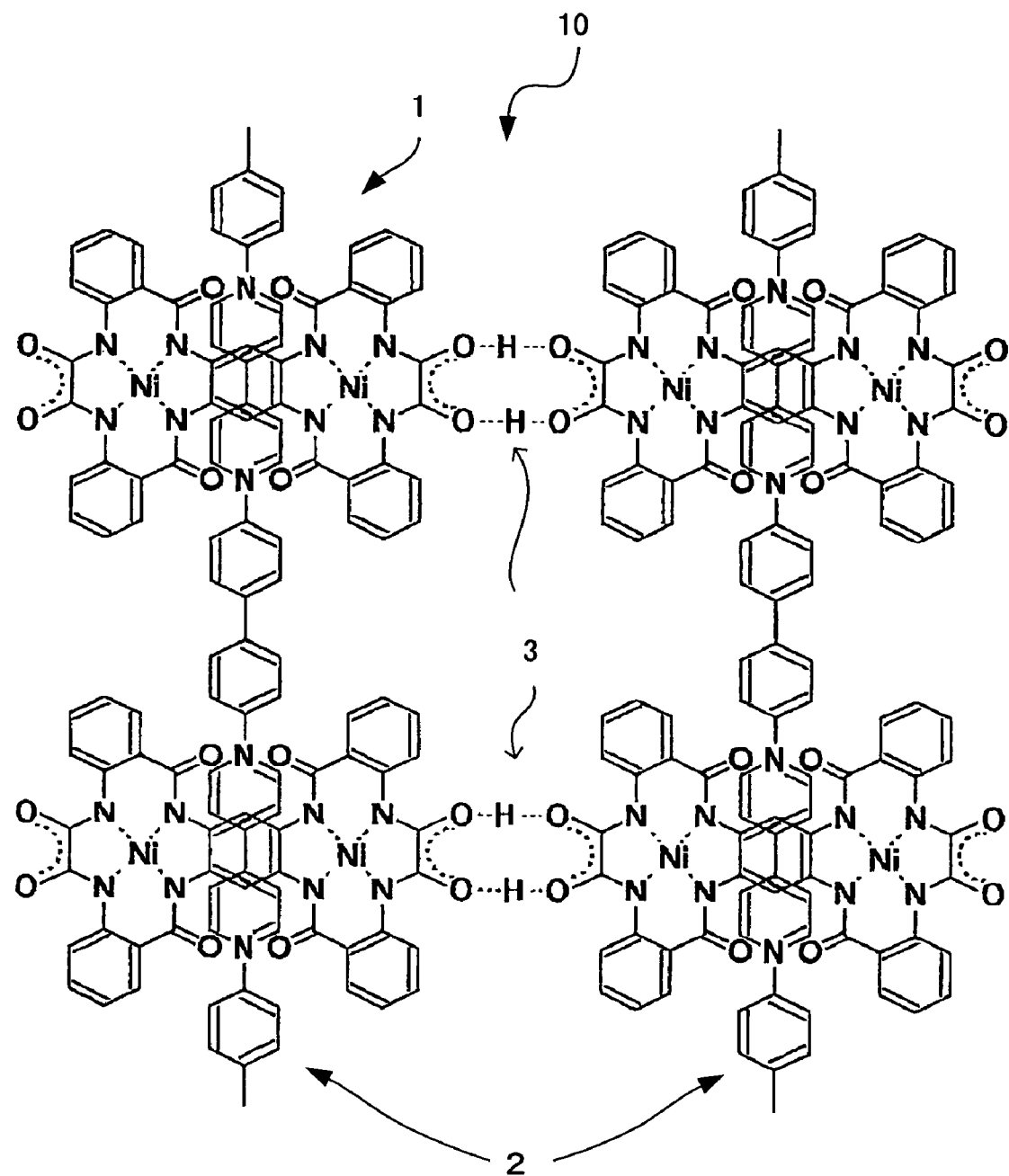
FIG. 6 is an explanatory schematic view of an example of a matrix circuit comprising a metal complex chain of a spin-ladder structure.

FIG. 6 is an explanatory schematic view of an example in which the metal complex chains in the matrix circuit are the spin-ladder metal complex chains. In the matrix circuit 10 shown in FIG. 6, the metal complex chains 1 having a spin-ladder structure each constitute an electroconductive path in a direction in between adjacent metal complex chains by the action of hydrogen bonding 3 between the adjacent metal complex chains. Electroconductive wires 2 each containing the molecule serving as an acceptor intersect with the metal complex chains 1. The resulting matrix circuit 10 has a three-dimensional network structure shown in FIG. 6. The three-dimensional network structure in the matrix circuit 10 is a single crystal or thin film formed by self-assemblage of the metal complex chains 1. The electroconductive wires 2 containing the molecules serving as an acceptor and the electroconductive paths formed in a direction in between the metal complex chains extend and reach edges of the single crystal or thin film.

Figure 8:
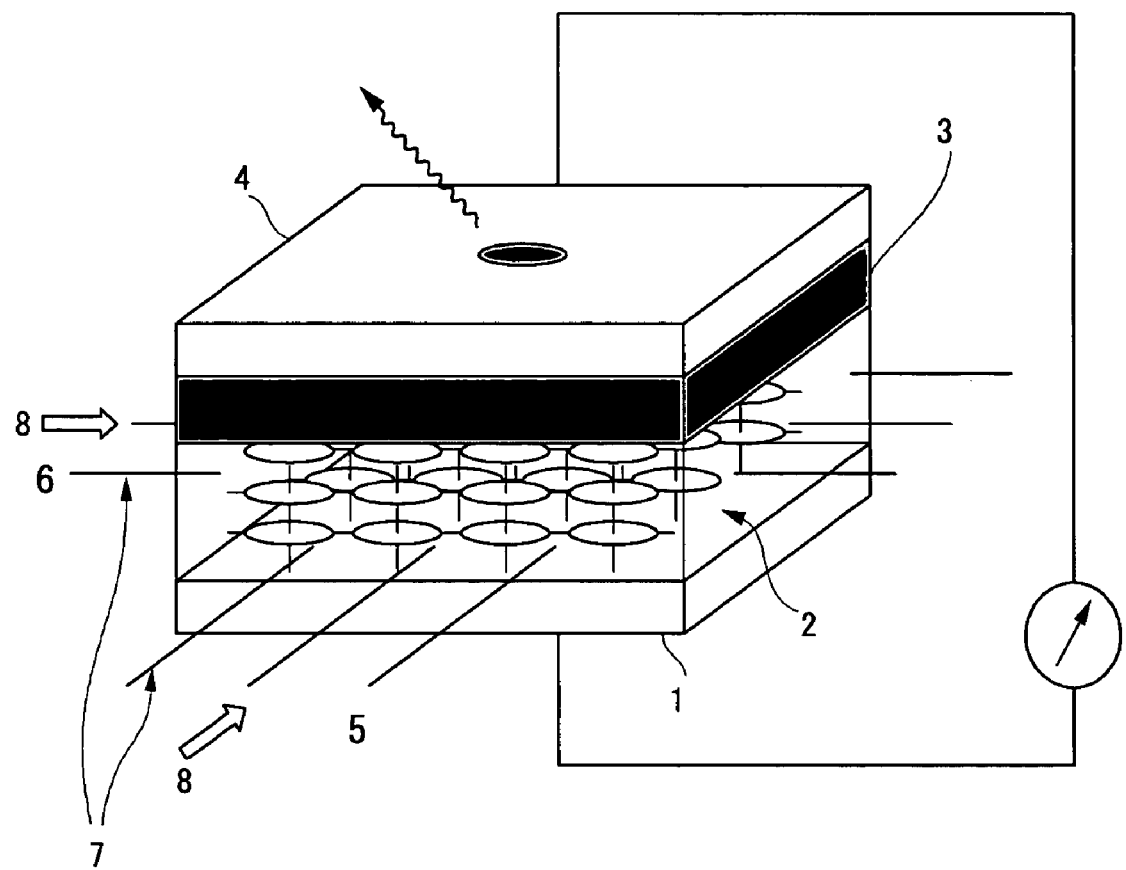
FIG. 8 is an explanatory schematic view of an example of a display having a substrate and a layer which is arrayed on or above the substrate and is controlled to emit light by the action of a current from a matrix circuit. The display is prepared by forming a multilayer thin film on the substrate, stacking a light-emitting molecule layer thereon, and covering the light-emitting molecule layer with an optically transparent electrode plate.

Individual metal complex molecules in the metal complex chains 1 are used as molecular devices. The acceptor-molecule-containing electroconductive wires 2 and the electroconductive paths formed in between the adjacent metal complex chains are used as address lines in X- and Y-directions, respectively, as shown in FIG. 8, and are connected to electrode terminals in the X- and Y-axes to have the function of transporting input/output signals to the individual molecular devices. Thus, the individual molecular devices at intersection points can be independently controlled to turn ON or OFF by inputting electric fields in the X- and Y-axes. In the stacked structure shown in FIG. 8, the lowermost layer is a substrate electrode 1, an upper layer of the substrate electrode is a matrix layer 2, a further upper layer thereof is a light-emitting molecule layer 3, and the uppermost layer is an optically transparent electrode 4. The arrow extending upward from the uppermost layer represents light emission, and straight lines extending along the X- axis 5 or the Y-axis 6 represent address lines 7. The arrows 8 represent input.

By imparting an electroconductive interaction to between the metal complex chains in a direction substantially perpendicular to the assembling direction (interchain direction), a fine matrix circuit on the molecular level can be provided.

<Molecular Functional Device>

The metal complex assembly of the present invention has the above-mentioned structure and functions and is applicable to a molecular functional device. The molecular functional device preferably has a multilayer thin-film structure. The multilayer thin-film structure comprises at least one component selected from the central metal ion and the ligand in the metal complex, the bridging ligand in the metal complex chain, and the molecule serving as at least one of an acceptor and a donor in the electroconductive wire, and the at least one component preferably comprises two or more different types of the component.

The multilayer thin-film structure can be prepared by any suitable process, such as a process of forming a multilayer film by repeating electrolytic synthesis or Langmuir-Blodgett (LB) technique.

The multilayer thin-film structure contributes to constitute a molecular functional device having a superlattice structure, in which two or more molecular layers having different functions are systematically stacked. This molecular functional device can control, molecule-by-molecule, at least one of functions of electron state changing or light emitting along therewith, storage, structure changing, and computing.

The metal complex chains in the molecular functional device may each have a terminal functional molecule that can interact with the metal complex chains.

Thus, the functional molecule can impart a noble function such as light emission, storage, structure change or computing to the molecular functional device, and the resulting molecular functional device having the novel function can be applicable typically to arithmetic and logic units, displays and memories.

Figure 7:
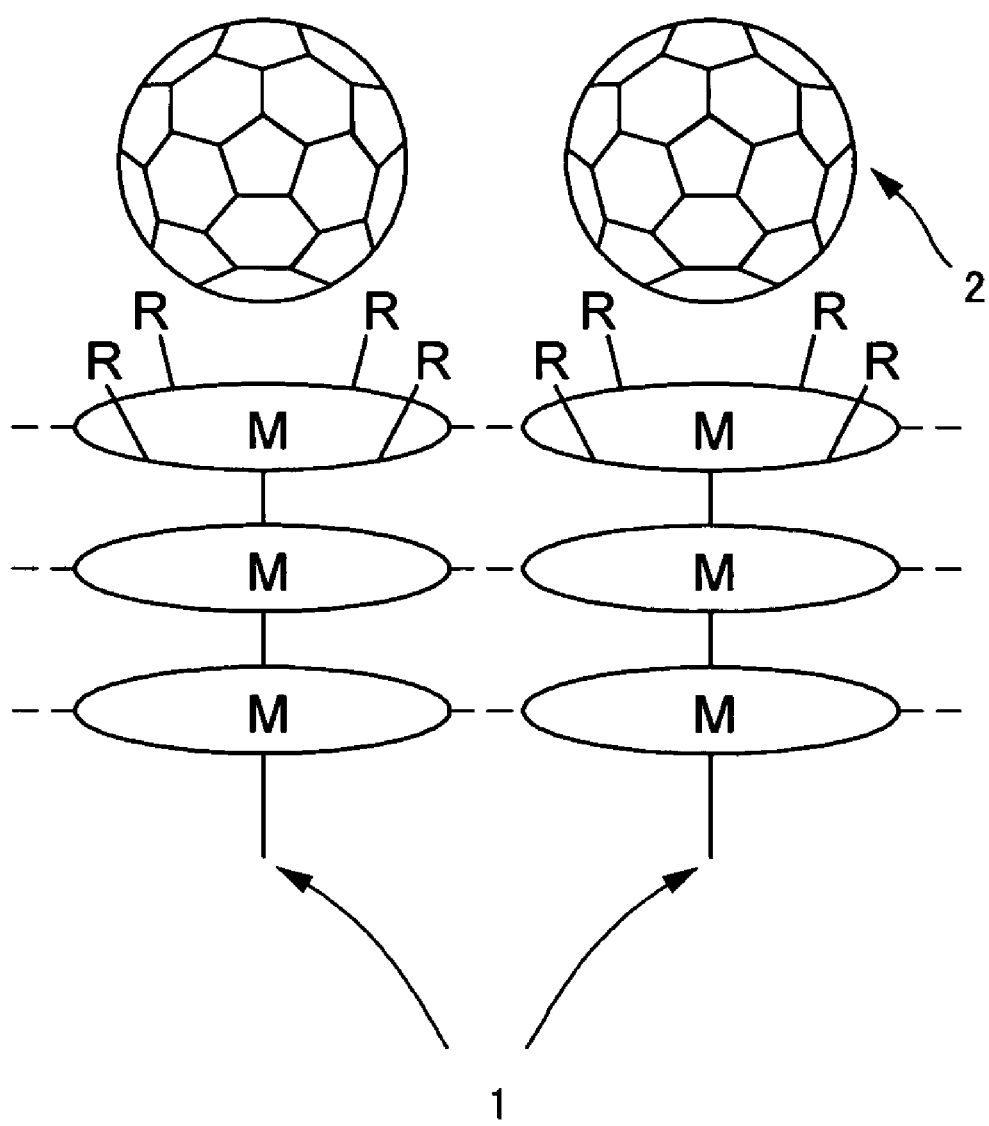
FIG. 7 is an explanatory schematic view of an example of metal complex chains, in which added terminal alkyl chains capture fullerene molecules.

FIG. 7 shows a specific example of the molecular functional device having the terminal functional molecule. In this example, the metal complex chain 1 comprising a straight line extending vertically and connecting ellipses including "M" in FIG. 7 has terminal alkyl chains (alkyl groups represented by "R" in FIG. 7). The alkyl groups capture a fullerene 2 represented by the soccer ball structure in FIG. 7.

FIG. 8 shows another specific example of the molecular functional device having the terminal functional molecule. This molecular functional device constitutes a display by stacking a light-emitting molecule layer and an optically transparent electrode in this order at one end of the metal complex chains and forming a substrate electrode at the other end. The display can emit light by action of electrification from the metal complex chain.

The display does not require electroconductive connections to the individual metal complex chains, can serve as a display only by passing current between the upper and lower electrode substrates and does not require microprocessing.

In addition, molecular functional devices having different functions can be designed by replacing the light-emitting molecule layer with, for example, a layer having variable optical properties, a layer having a variable molecular structure or a molecular recognition layer.

<Logical Circuit>

The metal complex assembly of the present invention has the above-mentioned structure and functions and is applicable to a logical circuit. The metal complex assembly has a structure in which the electroconductive wires extend and reach the edges of the single crystal or thin film. By dividing the terminal input section of, for example, the electroconductive wires in the metal complex assembly into plural regions and inputting electric fields to the individual regions, a fine logical circuit on the molecular level that can apply an output of a specific level in the extending direction of the metal complex chain can be designed.

Figures 9A, 9B:
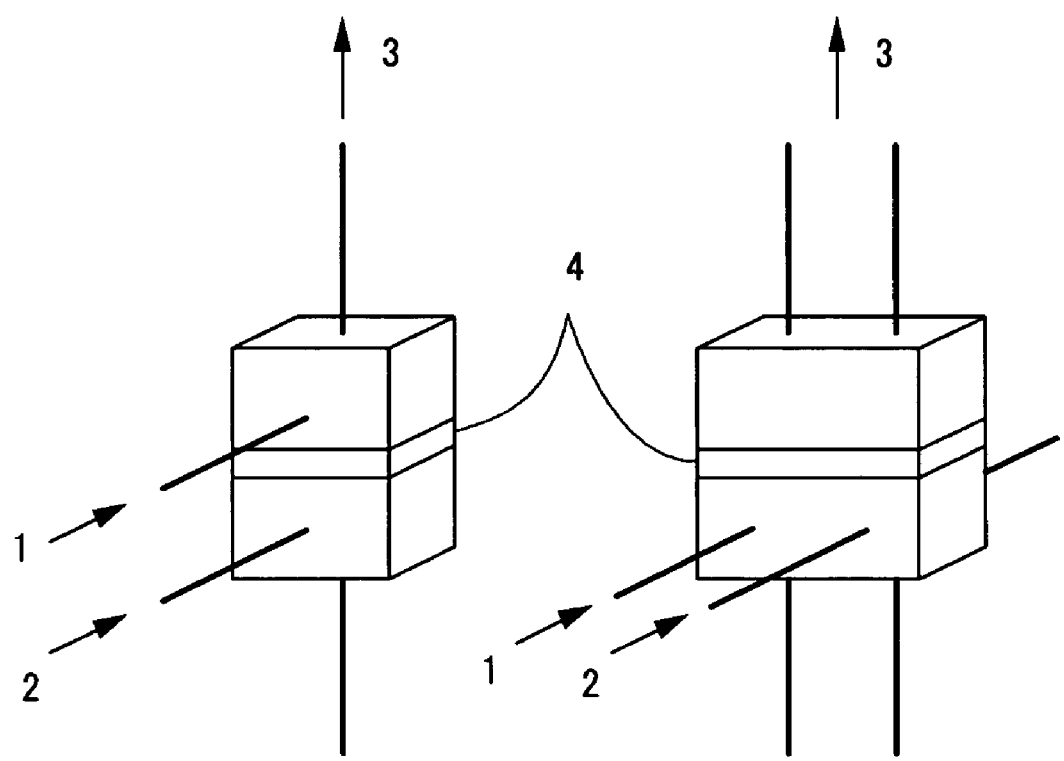
FIGS. 9A and 9B are schematic views of examples of logical circuits (AND circuit and OR circuit, respectively,) using the metal complex assembly of the present invention.

FIGS. 9A and 9B are explanatory schematic views, in which the metal complex assembly of the present invention is applied to an AND circuit (FIG. 9A) and an OR circuit (FIG. 9B) as logical circuits, respectively. In FIGS. 9A and 9B, the arrows pointing from the front to the back represent Input A and Input B, the arrows pointing upward represent Output C, and the inner layers in the three-layer structure represent interchain electroconductive layers 4. 1, 2, and 3 in FIGS. 9A and 9B represent Input A, Input B and Output C, respectively.

The logical circuit shown in FIG. 9A is divided into two regions along the extending direction of the metal complex chain and is so configured that electric fields are inputted (Input A and Input B) to the individual electroconductive wires, and a current in the extending direction of the metal complex chain is outputted (Output C). This logical circuit serves as an AND circuit which produces Output C only in the case when both Input A and Input B are inputted (FIG. 10A).

The logical circuit shown in FIG. 9B is divided in the extending direction of the metal complex chain into two regions by inserting an electroconductive layer between the metal complex chains. One of the two regions is further divided in the extending direction of the metal complex chain into two regions. Thus, the logical circuit is so configured that electric fields are inputted (Input A and Input B) to the individual regions and a current passing in an opposite direction to the interchain electroconductive layer (Output C). This logical circuit serves as an OR circuit which produces Output C in the case when at least one of Input A and Input B is inputted (FIG. 10B).

Thus, various logical circuits can be designed by changing the input mode of current.

The size of an arithmetic and logic unit (arithmetic element) in the logical circuit is determined depending on the accuracy in connection of electrode terminals. When a terminal is bound to the crystal using, for example, a paste, a multitude of molecules operate as a mass. When signals are applied to the individual molecular wires respectively using, for example, STM, the logical circuit constitutes a nanoscale device which operates on a molecule to molecule basis.

As is described above, the metal complex assembly of the present invention comprises the metal complex chains and the electroconductive wires intersecting with each other so as to interact with each other. Thus, it is applicable to nanoscale devices that provide molecular-level switching devices and wiring therebetween simultaneously and have very high functions. This is on the basis of operation and advantages of the self-assemblage of the metal complexes and resulting self-packing and realizes an electron circuit of the minimum scale that is physically achieved. The metal complex assembly of the present invention is prepared as a uniform lattice structure, can be advantageously driven at any stage from a molecular device comprising several molecules to an ultimate single-molecule device and is applicable to a device of a desired scale.

By stacking, as the metal complex chain, the polynuclear metal complex of the present invention comprising metal complexes having coordination sites linked with an aromatic ring, a donor or acceptor can be inserted into between the stacked layers. The resulting metal complex assembly of the present invention can more efficiently transfer charges and may promisingly exhibit novel electron states and functions. Thus, the use of the ladder structure metal complex chain having an intermediate properties between properties of one-dimensional and two-dimensional substances constitutes molecular wires that solve problems specific to the properties of low-dimensional substances, such as Peierls transition, and provides metal complex assemblies having high functions to constitute molecular devices. When the metal complex chain is the spin-ladder metal complex chain, the metal complex assembly is hopeful to exhibit high electroconductivity or superconductivity as a result of carrier doping.

The metal complex assembly of the present invention can be prepared according to a suitable procedure. For example, it can be prepared by crystallizing or forming a film of a solution containing the metal complex or polynuclear metal complex (assemblage metal complex) and the molecule serving as at least one of an acceptor and a donor according to at least one of electrolytic reaction (electrolytic synthesis) and Langmuir Blodgett technique.

In the electrolytic reaction (electrolytic synthesis), the metal complex or polynuclear metal complex (assemblage metal complex), the molecule serving as at least one of an acceptor and a donor and other components are dissolved in a solvent such as an alcohol, and the solution is subjected to electrolysis to deposit a metal complex assembly comprising assembled metal complex chains on a specific electrode.

For example, to prepare halogen-bridged metal complex chains having nickel as the central metal ion as the metal complex chains in the electrolytic reaction (electrolytic synthesis), nickel as the central metal ion is oxidized from divalent to trivalent to thereby form the metal complex chain. By reacting 4,4'-bipyridyl and a dibromoalkyl upon the formation of the metal complex chain, 4,4'-bipyridyl serves as an acceptor molecule and as a counter cation and thereby forms the electroconductive wire accompanied with the formation of the metal complex chain. In addition, hydrogen bonding between H and O—H in the metal complex interchain direction contributes to form the electroconductive wire and the electroconductive path in X- and Y-directions simultaneously. The bonding can be formed under relatively mild conditions and proceeds simultaneously with the formation of the metal complex chain by electrolytic synthesis. Thus, the bonding enables the self-alignment and self-assemblage of the metal complex chain in the interchain direction.

The metal complex assembly is preferably efficiently prepared by the method for producing a metal complex assembly of the present invention. According to this method, a polynuclear metal complex to be coordinated to a halogen ion as a bridging ligand, and a pi-conjugated planar molecule being halogenated at two or more positions are subjected to an electrolytic reaction. Then, the polynuclear metal complex includes the halogen ions as the bridging ligand to thereby form a one-dimensional chain. The pi-conjugated planar molecule undergoes electrolytic polymerization by the catalysis of the polynuclear metal complex. Thus, the one-dimensional chain formed from the polynuclear metal complex and the electroconductive wire formed from the pi-conjugated planar molecule are simultaneously formed by deposition or precipitation. Taking the electrolytic reaction (electrolytic synthesis) of a halogen-bridged nickel complex and a p-dibromoaryl as an example, the p-dibromoaryl is polymerized by the catalysis of the nickel complex to thereby form an electroconductive wire such as of poly-p-phenylene and, upon polymerization, releases bromine ions. The halogen-bridged nickel complex includes the released bromine ions as the bridging ligand to thereby form a one-dimensional metal complex chain. Herein, both the synthesis of the electroconductive wire and the formation of the one-dimensional metal complex chain serve as a complement to each other and thereby very efficiently proceed.

Examples of the electrode for use in the electrolytic reaction (electrolytic synthesis) are a platinum wire, platinum plate or glass plate having an indium tin oxide (ITO) film formed by vapor deposition. The supporting electrolyte for use herein may be, for example, tetrabutylammonium.

As a result of the crystallization or film formation, the metal complex (assemblage metal complex) and at least one of the donor molecule and acceptor molecule are self-assembled. The crystallization or film formation procedure can be repeated plural times in the present invention.

The metal complex assembly of the present invention can also be prepared by utilizing the properties of the metal complex to be regularly spontaneously arrayed and assembled in a solid due to its various interactions (chemical bonding or self-assemblage of molecules).

In this case, a metal complex assembly having a single-crystal or thin-film structure can be efficiently prepared. Together with the formation of the metal complex chain, the molecules serving as at least one of an acceptor and a donor are arrayed so as to allow electric conduction due to its interaction such as a bonding to form the electroconductive wire. Thus, a two-dimensional or three-dimensional network structure is formed in one process to thereby prepare the metal complex assembly having a single-crystal or thin film structure efficiently.

In the present invention, the metal complex assembly can be formed into, for example, a single crystal or thin film by suitably setting, for example, the production conditions and the combination of materials. A molecular device having a fine, uniform, precise and accurate structure can be efficiently prepared in a bottom-up manner by assembling the metal complex assembly as a basic unit.

In the production of the metal complex assembly of the present invention, the polynuclear metal complex of the present invention is typically preferably used as an assemblage metal complex for the following reasons.

The polynuclear metal complex of the present invention has a planar structure and comprises two central metal ions and two planar coordination sites being coordinated to the central metal ions in one plane in one molecule. By assembling the polynuclear metal complex having the planar structure as a building block, the metal complex assembly of strongly correlated electron system having a ladder structure and capable of developing the superconductive transition capability can be formed. To develop the superconductive transition capability, the antiferromagnetic spin array must be controlled and carriers must be doped thereinto. However, no success in carrier doping in a complex or a molecular ladder compound has yet been known.

The production of the metal complex assembly of the present invention uses the polynuclear metal complex comprising one ligand coordinated to two metal ions and thereby does not depend on a synthetic procedure or condition such as mixing ratio. In addition, it can easily form a ladder structure, can thereby easily chemically modify the ligand moiety and impart a variety of different functions to the resulting metal complex assembly.

The metal complex assembly of the present invention can contribute to the switching of current on the molecular level. The metal complex assembly is suitable for typically constituting molecular devices, matrix circuits, molecular functional devices and logical circuits capable of operating at ultrahigh density and ultrahigh speed, is applicable to the miniaturization and elaboration of devices and apparatus in information and communication fields, such as arithmetic and logic units, displays and memories and can thereby constitute nanoscale devices.

The present invention will be illustrated in further detail with reference to several examples below, which are not intended to limit the scope of the present invention.

EXAMPLE 1

A metal complex assembly having a matrix structure was formed as a single crystal on a platinum substrate by dissolving bis(ethylenediaminato)palladium complex, 4,4'-bipyridyl, a dibromoalkyl and tetrabutylammonium bromide (supporting electrolyte) in alcohol and subjecting the solution to electrolytic synthesis (electrolytic oxidation). The metal complex assembly contained one-dimensional metal complex chains shown in FIG. 1A in which the bromine ions serving as a bridging ligand and the bis(ethylenediaminato) palladium complexes were stacked in alternate order, and electroconductive wires intersecting with the metal complex chains formed as a result of the reaction between 4,4'-bipyridyl and the dibromoalkyl shown in FIG. 3.

EXAMPLE 2

A metal complex assembly containing a metal complex chain (the spin-ladder chain) of a two-leg ladder structure having two antiferromagnetic one-dimensional metal complex chains was constituted in the following manner. The metal complex assembly may realize a spin-ladder electron state.

Initially, multidentate ligand (bidentate ligand) comprising two planar macrocycles coupled through benzene ring was synthetically prepared by reacting anthranilic acid, oxalyl chloride and 1,2,4,5-benzenetetramine. The reaction product was mixed with nickel acetate and thereby yielded a polynuclear nickel(II) complex (polynuclear metal complex) shown in FIG. 2B.

Next, the above-prepared polynuclear nickel(II) complex, 4,4'-bipyridyl, dibromoalkyl and tetrabutylammonium bromide (supporting electrolyte) were dissolved in alcohol, and the solution was subjected to electrolytic synthesis (electrolytic oxidation) and thereby yielded a metal complex assembly on a platinum substrate. The metal complex assembly comprised assembled halogen-bridged nickel(III) complex chains (spin-ladder chains) having a ladder structure shown in FIG. 2A.

EXAMPLE 3

A metal complex assembly as a strongly correlated electron system was constituted in the following manner. In the metal complex assembly, one-dimensional metal complex chains have electrical properties similar to those of a superconductor.

A metal complex assembly of matrix structure was prepared by the procedure of Example 1, except for using bis (cyclohexanediaminato)nickel complex (FIG. 1B) as the metal complex instead of one used in Example 1.

The metal complex chain (bromine-bridged bis(cyclohexanediaminato)nickel(III) complexes) in the resulting metal complex assembly constitutes a one-dimensional assembly having one spin in $dz^2$ orbital, has a high on-site Coulomb repulsion of electron of about 5 eV and thereby exhibits the properties as a strongly correlated electron system. Thus, the metal complex assembly yielded a Mott insulator state which is expected to achieve superconductive transition as a result of carrier doping, as in a superconducting copper oxide known as a strongly correlated electron system.

EXAMPLE 4

The metal complex assembly obtained in Example 1 is a single crystal in which metal complex chains and electroconductive wires intersect each other and the electroconductive wires extend and reach edges of the single crystal.

The electroconductivity of the metal complex assembly was switched from insulation state to a metallic state or superconductive state by connecting an electrode terminal to the electroconductive wire, applying an electric field from outside of the single crystal, transmitting an electric signal, and thereby doping carriers into the metal complex chain. In contrast, the electroconductivity was switched from metallic or superconductive state to insulation state by changing the quantity of the applied electric field and thereby controlling the potential difference between the electroconductive wire and the metal complex chain. These results verify that charge transfer occurs between the electroconductive wire and the metal complex chain intersecting with each other, and that the resulting molecular device has a fine function as a switching device on the molecular level and can control electroconductivity in the extending direction of the metal complex chain even inside the single crystal.

EXAMPLE 5

A multidentate ligand (octadentate ligand) comprising two planar macrocycles coupled through benzene ring was synthetically prepared by reacting anthranilic acid, oxalyl chloride and 1,2,4,5-benzenetetramine. The reaction product was mixed with nickel acetate and thereby yielded a polynuclear nickel(II) complex.

Next, the above-prepared polynuclear nickel(II) complex, 4,4'-bipyridyl, a dibromoalkyl and tetrabutylammonium bromide (supporting electrolyte) were dissolved in alcohol, the solution was subjected to electrolytic synthesis (electrolytic oxidation) and thereby deposited a metal complex assembly on a platinum substrate. The metal complex assembly has a three-dimensional network structure composed of three-dimensionally assembled halogen-bridged nickel(III) complex chains (metal complex chains 1) having a ladder structure shown in FIG. 6.

The metal complex assembly is a single crystal formed by self-assemblage of the metal complexes (metal complex chains 1), in which the electroconductive wires 2 serving as an acceptor and electroconductive paths in the metal complex interchain direction extend and reach the edges of the single crystal. Thus, individual metal complex molecules in the metal complex chains 1 were used as molecular devices, and the electroconductive wires 2 serving as an acceptor and the electroconductive path coupled in an interlayer direction of the metal complexes were used as address lines in X- and Y-directions as shown in FIG. 8. Then electrode terminals in X- and Y-directions were connected to thereby allow the individual devices to transmit input/output signals. By inputting an electric field in X- and/or Y-direction, the respective molecular devices positioned at the intersection point could be switched to turn ON/OFF independently and separately.

EXAMPLE 6

The electrolytic synthesis (electrolytic oxidation) procedure of Example 1 was repeated, except for further using bis(cyclohexanediaminato)nickel(III) complex as the metal complex in combination with one used in Example 1. Thus, a multilayer thin-film metal complex assembly was formed on a platinum substrate. The metal complex assembly has a structure in which a one-dimensional metal complex chain shown in FIG. 1A and a one-dimensional metal complex chain shown in FIG. 1B are assembled, and electroconductive wires intersect with the two different metal complex chains. It was verified that a matrix circuit having a superlattice structure was efficiently constituted by systematically stacking (assembling) molecular layers having different functions.

EXAMPLE 7

A display was prepared by forming a light-emitting molecule layer on the metal complex assembly on the platinum substrate prepared according to Example 6, and covering the surface of the light-emitting molecule layer with an optically transparent electrode plate (FIG. 8). The display can emit light by the action of electrification from the matrix circuit and control the light emission. In the display, a one-dimensional metal complex column to emit light can be designated molecule-by-molecule by the action of the matrix circuit, and light can be emitted only by electrifying the upper and lower electrode plates. Thus, the display did not require microprocessing.

EXAMPLE 8

The single-crystal metal complex assembly prepared in Example 1 was found to function as an AND circuit and OR circuit shown in FIGS. 9A, 9B, 10A and 10B, by dividing the terminal input section of the electroconductive wire extending and reaching the edges of the single crystal, and inputting electric fields to the individual sections.

EXAMPLE 9

<Preparation of 1,2:4,5-bis(4',8',9',13'-tetraoxo-5',6':11',12'-dibenzo-3',7',10',14'-tetraazacy clotetradecyl)-benzene Ligand (multidentate ligand) and a Polynuclear Metal Complex Containing the Same>

The carboxyl group of anthranilic acid was protected by esterification, the protected anthranilic acid was reacted with oxalyl chloride and thereby yielded a white precipitate. This was deprotected by saponification, was mixed with benzenetetramine and dicyclohexylcarbodiimide (DCC) and thereby yielded 1,2:4,5-bis(4',8',9',13'-tetraoxo-5',6':11',12'-dibenzo-3',7',10',14'-tetraazancy clotetradecyl)-benzene ligand (multidentate ligand). The ligand was mixed with tetrabutylammonium hydroxide and nickel acetate in methanol and thereby yielded a polynuclear nickel(II) complex as illustrated in the following formula.

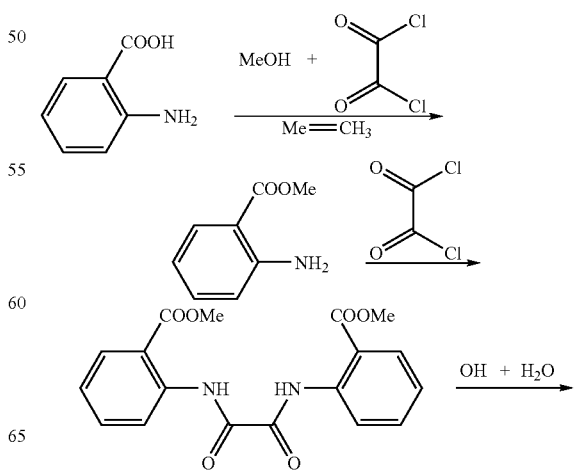

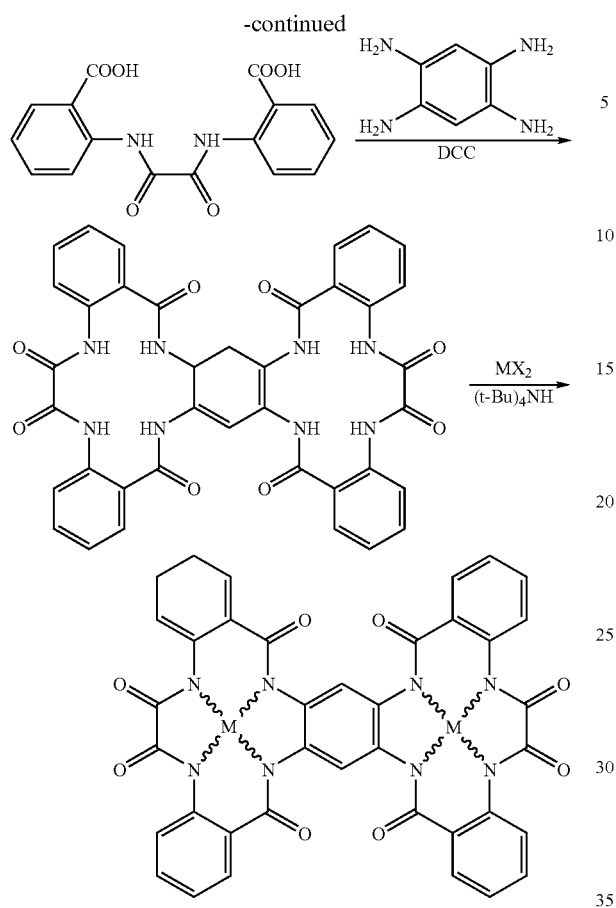

EXAMPLE 10

<Preparation of 1,2:4,5-bis(8'9'-dioxo-5',6':11',12'-dibenzo-3',7',10',14'-tetraazacyclotetra deca-3',13'-dienyl)-benzene Ligand (multidentate ligand) and a Polynuclear Metal Complex Containing the Same>

By reacting 2-aminobenzaldehyde, oxalyl chloride and 1,2,4,5-benzenetetramine, 1,2:4,5-bis(8'9'-dioxo-5',6':11', 12'-dibenzo-3',7',10',14'-tetraazacyclotetra deca-3',13'-dienyl)-benzene ligand (multidentate ligand) was prepared. This ligand comprises two planar macrocycles coupled with each other through benzene ring. The ligand was reacted with nickel acetate and thereby yielded a polynuclear nickel(II) complex as illustrated in the following formula.

EXAMPLE 11

<Preparation of 1,2,4,5-tetra(2-aminobenzamido)benzene Ligand (Multidentate Ligand) and a Polynuclear Metal Complex Containing the Same>

The amino group of anthranilic acid was protected by t-butoxycarbonyl (Boc) group, and the protected product was reacted with benzenetetramine and dicyclohexylcarbodiimide (DCC). The reaction product was deprotected by treating with trifluoroacetic acid and thereby yielded 1,2,4,5-tetra(2-aminobenzamido)benzene ligand (multidentate ligand). The ligand was mixed with nickel acetate in methanol with heating and stirring and thereby yielded a polynuclear nickel(II) complex as illustrated in the following formula.

-continued

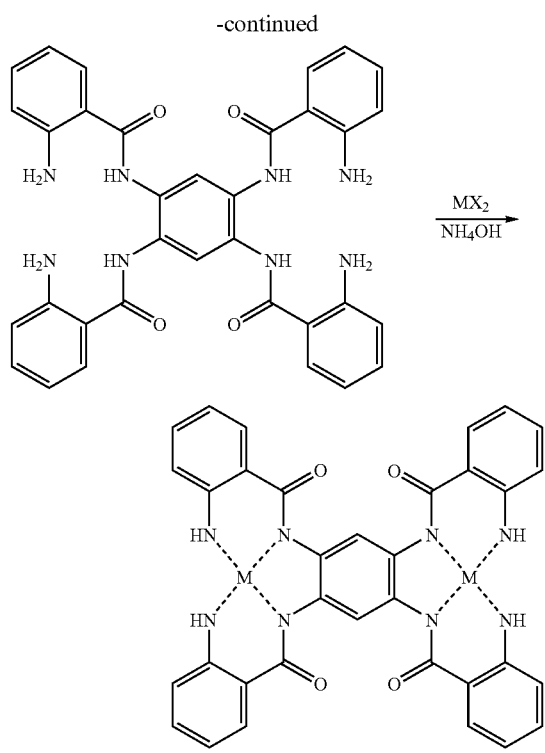

EXAMPLE 12

<Preparation of 1,2,4,5-tetra(2-aminobenzylideneamino) benzene Ligand (Multidentate Ligand) and a Polynuclear Metal Complex Containing the Same>

An orange precipitate of 1,2,4,5-tetra(2-aminobenzylideneamino)benzene ligand (multidentate ligand) was formed by mixing o-aminobenzaldehyde and benzenetetramine in alcohol. The orange precipitate was reacted with nickel acetate and thereby yielded a polynuclear nickel(II) complex as illustrated in the following formula.

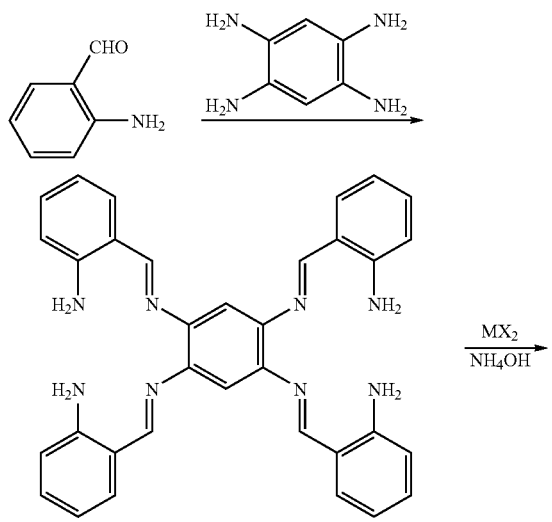

-continued

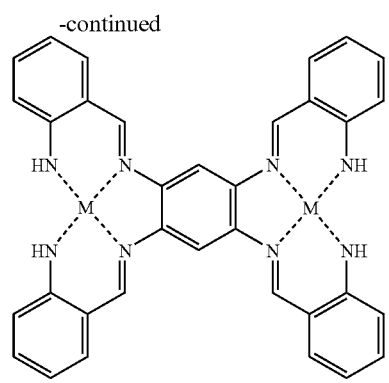

EXAMPLE 13

<Preparation of 1,2,4,5-tetra(pyridine-2-carboxamido)benzene Ligand (Multidentate Ligand) and a Polynuclear Metal Complex Containing the Same>

In an atmosphere of nitrogen gas, pyridinecarboxylic acid was mixed with benzenetetramine in pyridine as a solvent, was further mixed with triphenyl phosphite with heating at 100° C. for 4 hours and thereby yielded 1,2,4,5-tetra(pyridine-2-carboxamido)benzene ligand (multidentate ligand) as a white precipitate. The ligand was mixed with tetrabutylammonium hydroxide and nickel acetate in dimethylformamide and thereby yielded a polynuclear nickel(II) complex as illustrated in the following formula.

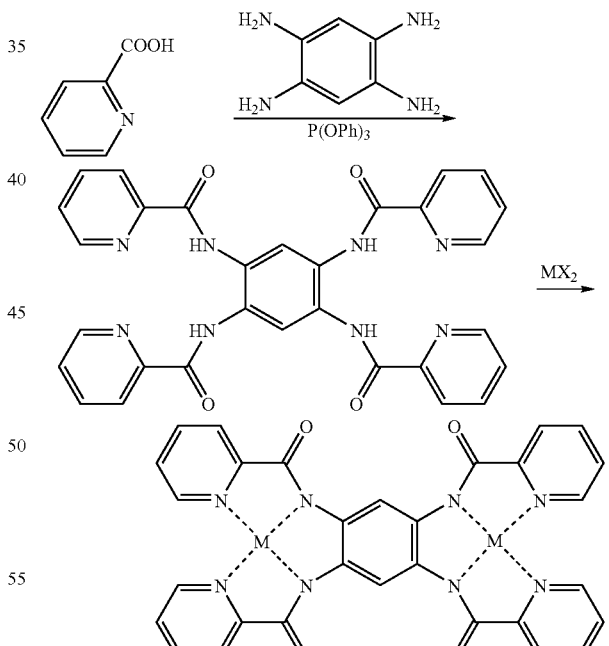

EXAMPLE 14

<Preparation of 1,2,4,5-tetra(2-pyridylmethylideneamino) benzene Ligand (Multidentate Ligand) and a Polynuclear Metal Complex Containing the Same>

In an atmosphere of nitrogen gas, pyridinecarbaldehyde and 1,2,4,5-benzenetetramine were mixed with triethylamine in methanol as a solvent and thereby yielded 1,2,4,5-tetra(2-pyridylmethylideneamino)benzene ligand (multidentate ligand) as an orange precipitate. The orange precipitate was reacted with nickel acetate in methanol and thereby yielded a polynuclear nickel(II) complex as illustrated in the following formula.

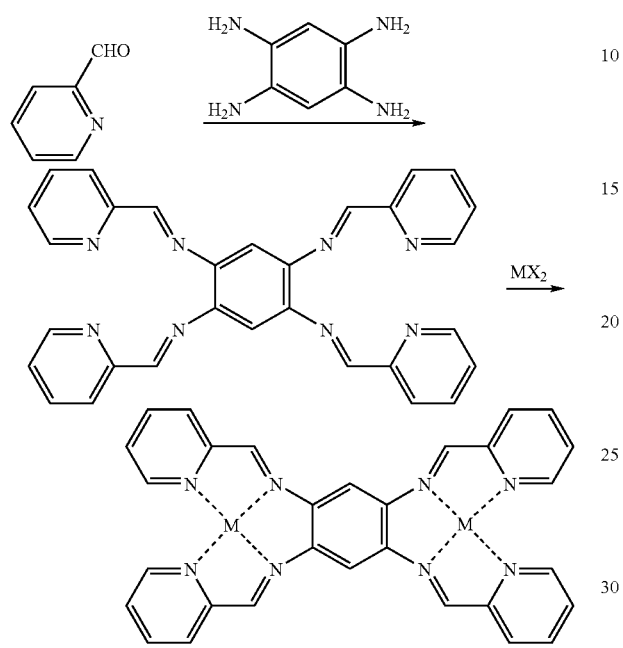

EXAMPLE 15

In each of the metal complexes prepared in Examples 9 to 14, the nickel ion serving as the central metal ion has an oxidation number of 2, and these metal complexes are each a single planar complex which is not stacked. To constitute a ladder structure by stacking the planar complex as a chain, the nickel ion must be oxidized to have an oxidation number of 3. This oxidation can be effectively carried out by electrolytic synthesis (electrolytic oxidation).

Each of the nickel(II) complexes prepared in Examples 9 to 14 and an excess amount of tetra-n-butylammonium bromide as a supporting electrolyte were dissolved in anhydrous methanol, nitrogen gas was bubbled into the solution to eliminate dissolved oxygen, and a constant current of 20 µA was allowed to pass therethrough using a platinum electrode to carry out electrolytic synthesis. In any of the nickel(II) complexes, bromine ions serving as a bridging ligand were coordinated to and sandwiched the nickel planar complex to form a chain structure. Thus, a single crystal of a metal complex assembly comprising an oxidized nickel(III) complex was precipitated on a positive electrode. The bridging ligand can be replaced with another type by changing the type of the supporting electrolyte (FIG. 2A and FIG. 2B).

EXAMPLE 16

Each of the metal complex assemblies prepared in Example 15 can include a planar dopant molecule also serving as a counter ion by sandwiching the same between the central aromatic ring in the polynuclear metal complexes.

The electrolytic synthesis procedure of Example 15 was repeated, except for using 4,4'-dimethylbipyridinium bromide as the supporting electrolyte in precipitation of a single crystal of metal complex assembly containing the nickel(II) complex prepared in Example 1. The resulting metal complex assembly has a ladder structure and comprises polynuclear nickel complexes and bromine ions serving as a bridging ligand, in which dimethylbipyridinium as a counter cation is included between layers. In the metal complex assembly, dimethylbipyridinium (acceptor molecule) forms pi-pi stacking with the benzene ring moiety at the center of the polynuclear nickel complex, and positively charged nitrogen atoms of bipyridinium interact with the negatively polarized carbonyl groups of the polynuclear nickel complex, as illustrated in the following formula.

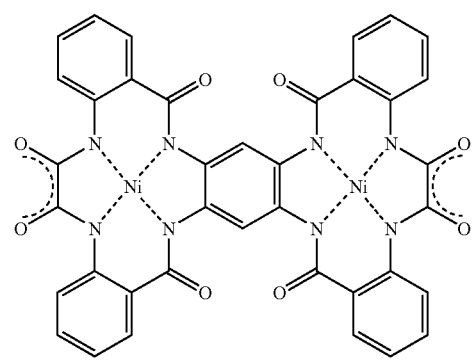

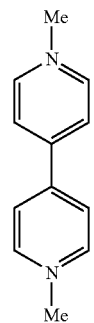

EXAMPLE 17

<Preparation of 1,2,4,5-tetra(3-aminopropanamido)benzene Ligand (Multidentate Ligand) and a Polynuclear Nickel(II) Complex Containing the Same>

The amino group of β-alanine was protected by t-butoxycarbonyl (Boc) group, and the protected compound was reacted with benzenetetramine, water-soluble carbodiimide (WSC) serving as a dehydration condensation agent, and 1-hydroxybenzotriazole (HOBT). Next, the reaction product was treated with trifluoroacetic acid (TFA) to eliminate the t-butoxycarbonyl (Boc) group and thereby yielded 1,2,4,5-tetra(3-aminopropanamido)benzene ligand (multidentate ligand). Prepared 1,2,4,5-tetra(3-aminopropanamido)benzene ligand (multidentate ligand) was mixed with aqueous ammonia and nickel acetate in methanol and thereby yielded a polynuclear nickel(II) complex having the following structure.

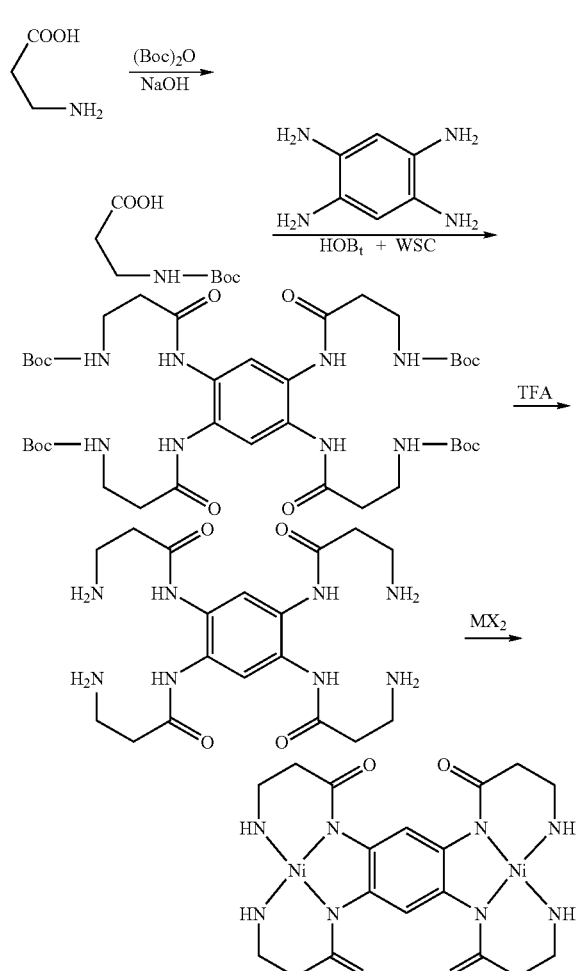

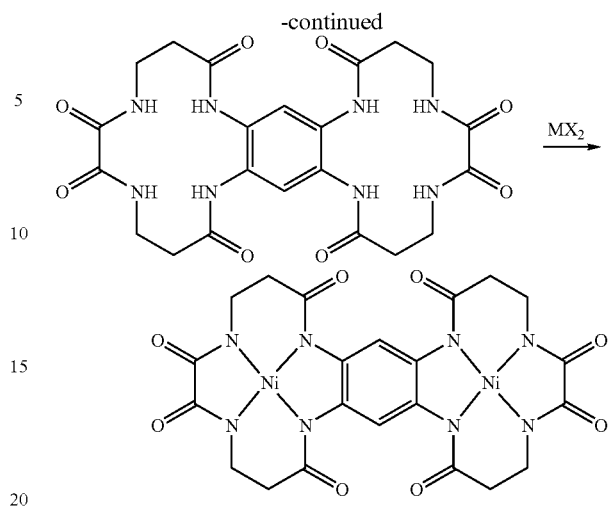

EXAMPLE 18

<Preparation of 1,2:4,5-bis(4',8',9',13'-tetraoxo-3',7',10',14'-tetraazacyclotetradecyl)-benz ene Ligand (Multidentate Ligand) and a Polynuclear Nickel(II) Complex Containing the Same>

The procedure of Example 17 was repeated, except for reacting 1,2,4,5-tetra(3-aminopropanamido)benzene ligand with oxalyl chloride and triethylamine, to thereby yield 1,2:4,5-bis(4',8',9',13'-tetraoxo-3',7',10',14'-tetraazacyclotetradecyl)-benz ene ligand in which two planar macrocycle are coupled with each other through benzene ring. The ligand was then reacted with nickel acetate and thereby yielded a polynuclear nickel(II) complex.

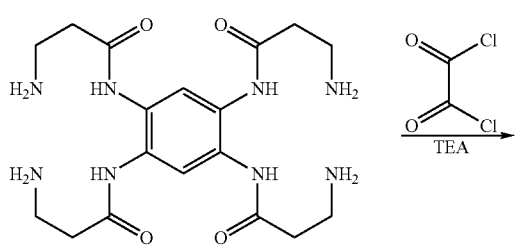

EXAMPLE 19

<Preparation of 1,2:4,5-bis(4',8',9',13'-tetraoxo-3',7',10',14'-tetraazacyclotetradeca-5'11'-di enyl)-benzene Ligand (Multidentate Ligand) and a Polynuclear Metal Complex Containing the Same>

The polynuclear nickel(II) complex comprising the 1,2:4,5-bis(4',8',9',13'-tetraoxo-3',7',10',14'-tetraazacyclotetradecyl)-benz ene ligand prepared in Example 18 was oxidized by heating and stirring in DMF with aeration and thereby yielded a planar polynuclear metal complex.

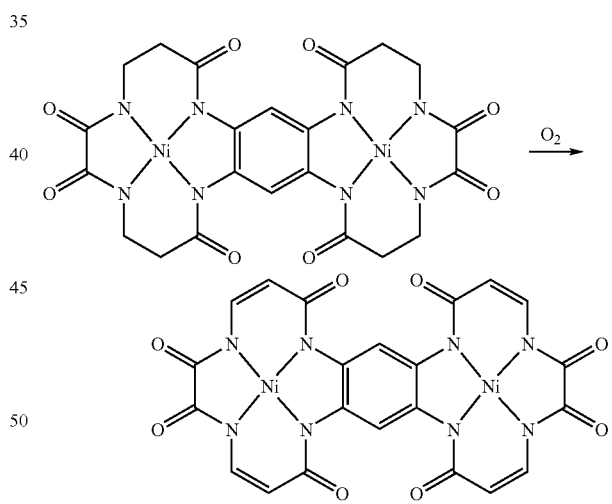

EXAMPLE 20

Each of the polynuclear metal complexes prepared in Examples 17 to 19 has nickel having an oxidation number of 2 as the central metal ions and is a planar metal complex which is not stacked. To constitute a ladder structure by stacking the metal complex as a chain, the nickel was oxidized to have an oxidation number of 3 by the following electrolytic synthesis technique.

Specifically, each of the nickel(II) complexes and an excess amount of tetra-n-butylammonium bromide as a supporting electrolyte were dissolved in anhydrous methanol, nitrogen gas was bubbled into the solution to eliminate dissolved oxygen, and a constant current of 20 μA was allowed to pass therethrough using a platinum electrode to carry out electrolytic synthesis. In any of the nickel(II) complexes, bromine ions serving as a bridging ligand coordinated with and sandwiched the nickel planar complex to form a chain structure, and as a result, a single crystal of a metal complex assembly comprising an oxidized polynuclear nickel(III) complex was precipitated on a positive electrode. The bridging ligand can be replaced with another type by changing the type of the supporting electrolyte.

EXAMPLE 21

The metal complex assembly prepared in Example 20 was allowed to include a planar dopant molecule serving as a counter ion by sandwiching the same between the aromatic rings in the stacked polynuclear metal complexes. More specifically, a crystal of a ladder nickel complex was prepared by the procedure of Example 1, except for dissolving 4,4'-dimethylbipyridinium bromide as the supporting electrolyte and subjecting the solution to electrolytic synthesis in the assemblage of the nickel complex. In the ladder nickel complex, bromine ions serve as a bridging ligand, and dimethylbipyridinium serving as a counter cation is included in between the layers.

EXAMPLE 22

Figure 13:
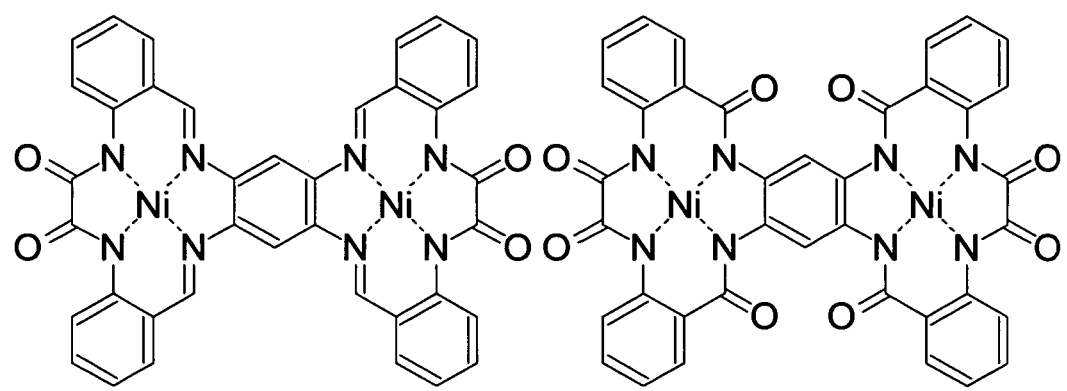
FIG. 13 is a view of an example of the structure of a polynuclear nickel complex having a planar structure.

A polynuclear nickel complex containing 1,2,4,5-tetra(2-aminobenzylideneamino)benzene ligand (multidentate ligand) (FIG. 13), carboxyl-containing p-quaterphenylene and pyrazine were dissolved in methanol in proportions of 1:1:2, and the solution was subjected to electrolytic synthesis (electrolytic oxidation) to thereby precipitate a single crystal of a metal complex assembly on an electrode.

Figure 14:
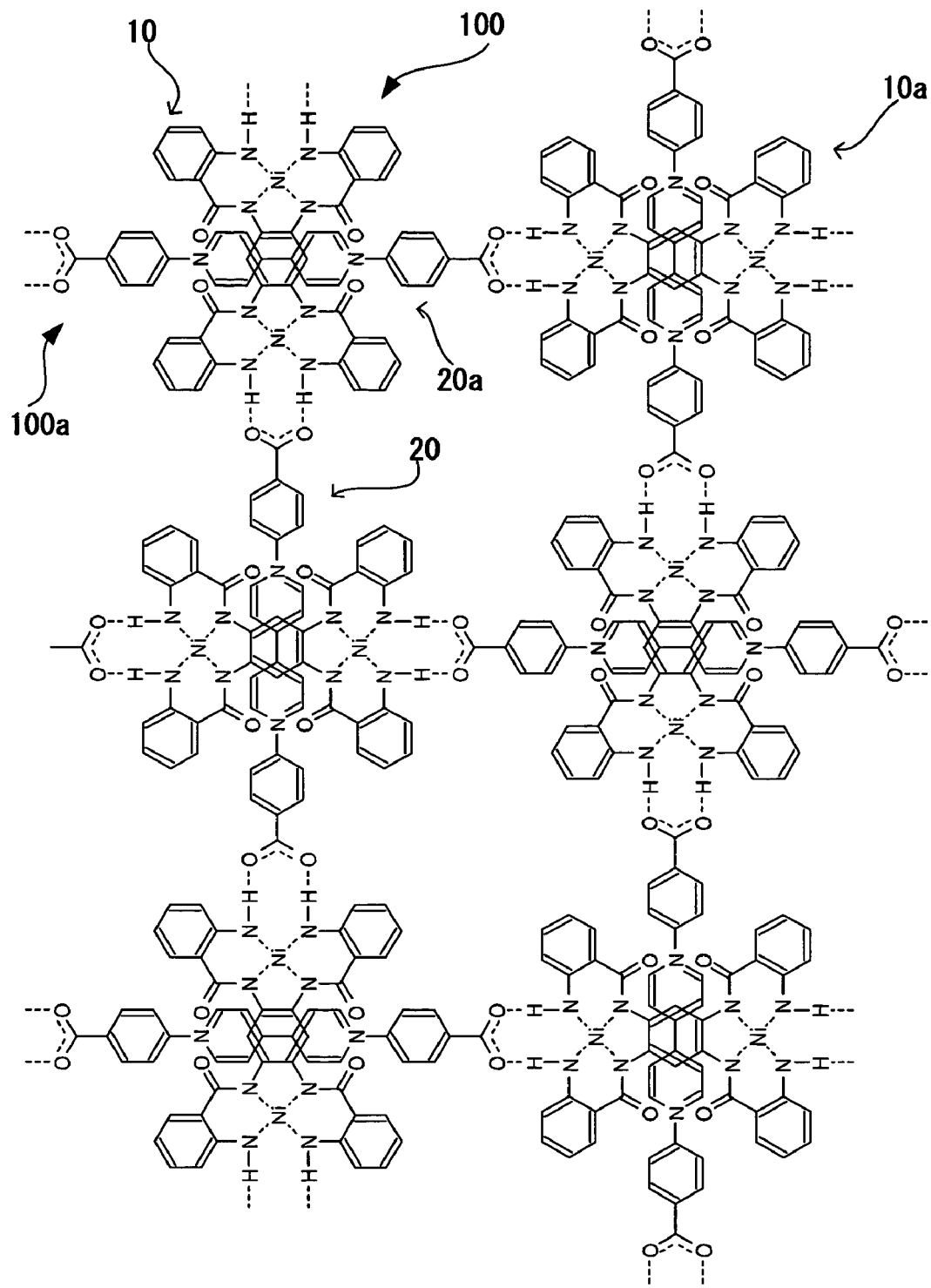
FIG. 14 is a schematic view of an example of the metal complex assembly having a three-dimensional network and comprising assembly containing one-dimensional chains intersecting with each other, which one-dimensional chains each comprise polynuclear nickel complexes and tetraphenylene molecules including a bipyridine structure being coupled in alternate order through hydrogen bonding.

In the metal complex assembly, planar polynuclear nickel complexes 10, pi-conjugated molecules 20 capable of serving as an acceptor (bipyridinium) were coupled through hydrogen bonding to thereby form one-dimensional chain 100 having a ladder structure and comprising metal complexes in the same plane as the coordination plane (FIG. 14). The polynuclear nickel complex 10 in the one-dimensional chain 100 includes a macrocycle having a functional group such as carbonyl group and can be coupled with another organic compound having a functional group such as hydroxyl group or amino group in one plane by the action of interactions such as hydrogen bonding. Nickel ions in the one-dimensional chain 100 were stacked in a vertical direction through the bridging ligands such as pyrazine, and an assembly of polynuclear metal complexes having a ladder structure was formed.

In the metal complex assembly, one-dimensional chains 100 and the metal complexes having a ladder structure penetrated each other, and molecular wires were arranged three-dimensionally orthogonally to thereby form a three-dimensional network. In other words, the single crystal comprised the one-dimensional chains 100 orthogonally intersecting with the one-dimensional chains 100a (FIG. 14). The one-dimensional chains 100 each comprised the polynuclear nickel complexes 10 and pi-conjugated molecules 20 coupled with each other in alternate order through hydrogen bonding. The one-dimensional chains 100a each comprised polynuclear nickel complexes 10a and pi-conjugated molecules 20a coupled with each other in alternate order through hydrogen bonding. The pi-conjugated molecules 20a in the one-dimensional chains 100a penetrated at the center part of the polynuclear nickel complexes 10 in the one-dimensional chains 100. The pi-conjugated molecules 20 in the one-dimensional chains 100 penetrated at the center part of the polynuclear nickel complexes 10a in the one-dimensional chains 100a.

In addition, pi-conjugated molecules serving as an acceptor 20 (bipyridinium) in the one-dimensional chains 100 constituted pi-pi stacking with the benzene ring moieties at the center part of polynuclear nickel complexes 10a in the one-dimensional chains 100a. The positively charged nitrogen atoms in the bipyridinium interacted with the negatively polarized carbonyl groups of the polynuclear nickel complexes 10a. Likewise, pi-conjugated molecules serving as an acceptor 20a (bipyridinium) in the one-dimensional chains 100a constituted pi-pi stacking with the benzene ring moieties at the center part of polynuclear nickel complexes 10 in the one-dimensional chains 100. The positively charged nitrogen atoms in the bipyridinium interacted with the negatively polarized carbonyl groups of the polynuclear nickel complexes 10.

Thus, charge transfer is accelerated, the electroconductive switch in the one-dimensional chain 100 or 100a works, and the circuit is ON, when an intersection point of an address line to which a negative potential is applied is constituted by the pi-conjugated molecule 20 or 20a (acceptor molecule) and another intersection point of an address line to which a negative potential is applied is constituted by the polynuclear nickel complex 10 or 10a. The intersection point of an address line is the intersection point between the polynuclear nickel complex 10 and the pi-conjugated molecule 20a (acceptor molecule) or the intersection point between the polynuclear nickel complex 10a and the pi-conjugated molecule 20 (acceptor molecule). In contrast, the charge transfer is inhibited, the switching does not work, and the circuit is OFF when an intersection point of an address line to which a negative potential is applied is constituted by the pi-conjugated molecule 20 or 20a (acceptor molecule).

In the metal complex assembly, the molecular wires orthogonally intersecting with each other are composed of identical one-dimensional chain 100 and one-dimensional chain 100a. Thus, the single crystal (three-dimensional structure) of the metal complex assembly has an isotropic symmetry, can be easily assembled, is stable and has an identical aspect ratio. In adjacent one-dimensional chains 100 and 100a, the polynuclear nickel complexes and the pi-conjugated molecules (acceptor molecules) are arranged in staggered order, in which a polynuclear nickel complex in one chain faces a pi-conjugated molecule in the other chain. Thus, the polarity of the potential to apply to the address lines is opposite between the adjacent one-dimensional chains. The metal complex assembly was found that it can avoid leakage of input signals to adjacent lines, thereby avoid misoperation and can be specifically advantageously applied to, for example, arithmetic and logic units, displays and memories. The leakage and resulting misoperation are concerns in conventional fine circuits.

EXAMPLE 23

Figure 15:
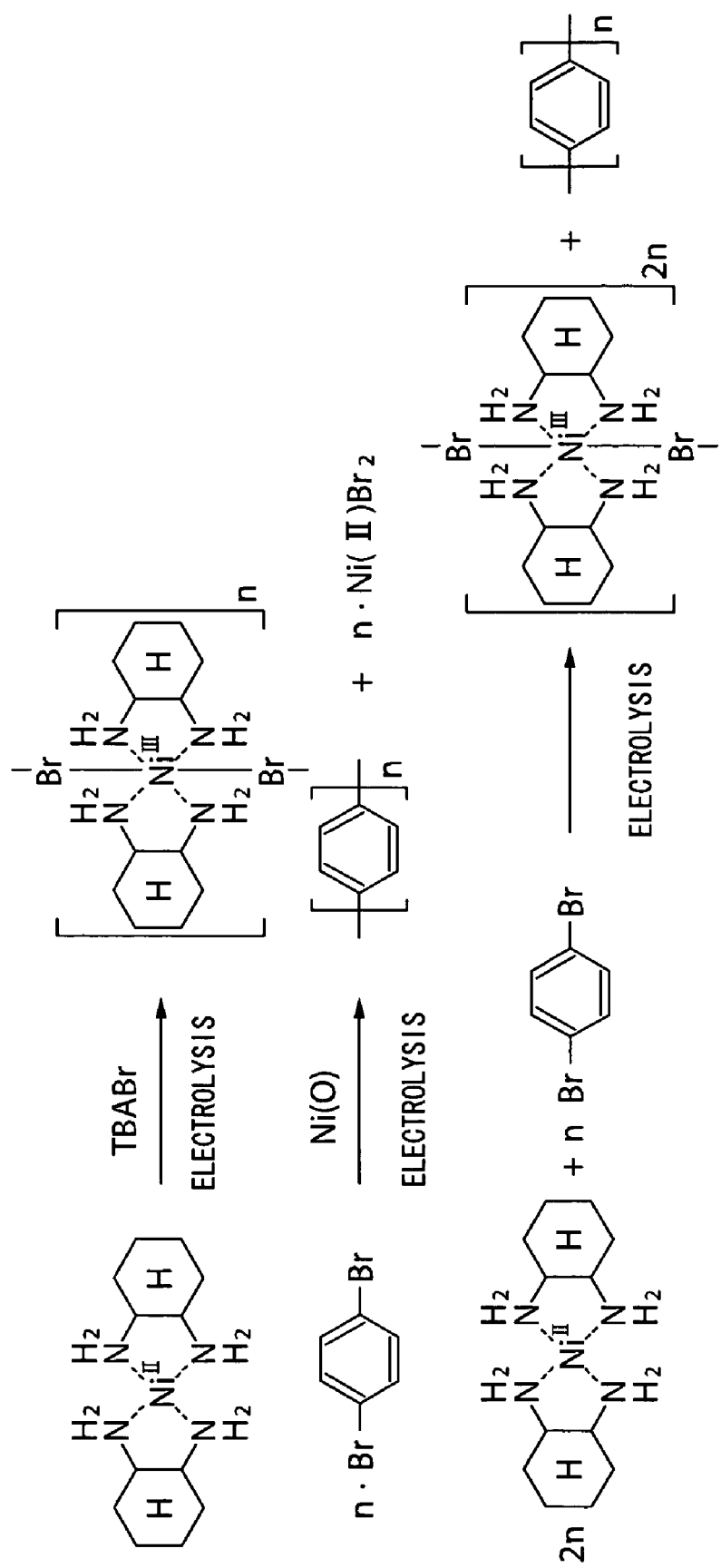
FIG. 15 is an example of reaction formulae, in which an electroconductive wire and a one-dimensional chain containing a polynuclear nickel complex are simultaneously formed as a result of electrolytic synthesis.

An electrolytic reaction (electrolytic synthesis) was carried out using a mixture solution of (cyclohexanediaminato)nickel(II) complex (polynuclear nickel complex) and p-dibromobenzene as a starting material. As a result, (cyclohexanediaminato)nickel(II) complex (polynuclear nickel complex) included bromine atoms as a bridging ligand to form a one-dimensional chain, and p-dibromobenzene underwent electrolytic polymerization by the catalysis of the nickel complex to thereby form poly-p-phenylene, an electroconductive polymer (FIG. 15). A compound was then precipitated. The compound comprised one-dimensional chains composed of the polynuclear nickel complexes, and poly-p-phenylene serving as an electroconductive wire. Thus, the one-dimensional chains composed of the polynuclear nickel complexes, and poly-p-phenylene serving as an electroconductive wire could be efficiently prepared in one process.

What is claimed is:

1. A multidentate ligand comprising two planar tetradentate coordination sites in one plane, wherein:
    each of the planar tetradentate coordination sites contains four nitrogen-containing groups selected from among at least one of imino, amido and amino groups and has the nitrogen atoms of the four nitrogen-containing groups as coordinating atoms in one plane,
    the multidentate ligand is represented by at least one of following Formulae (1) to (8):

Formula (1)

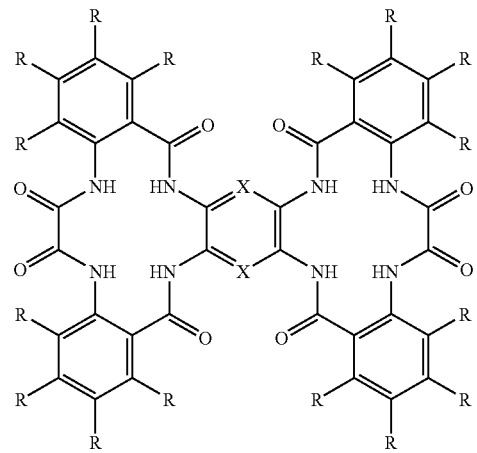

Formula (2)

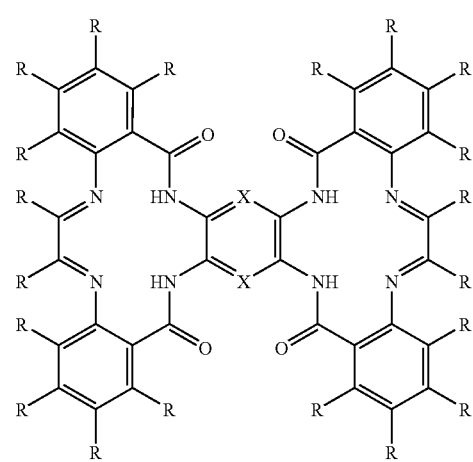

-continued

Formula (3)

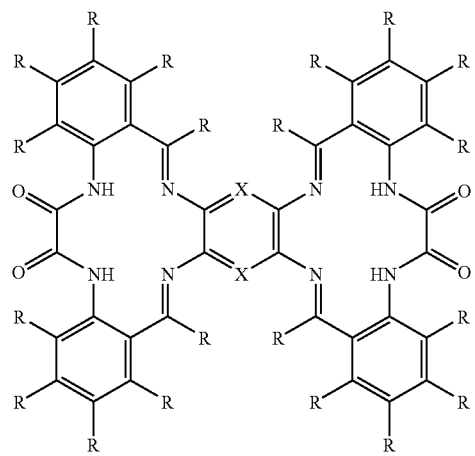

Formula (4)

Formula (5)

-continued

Formula (6)

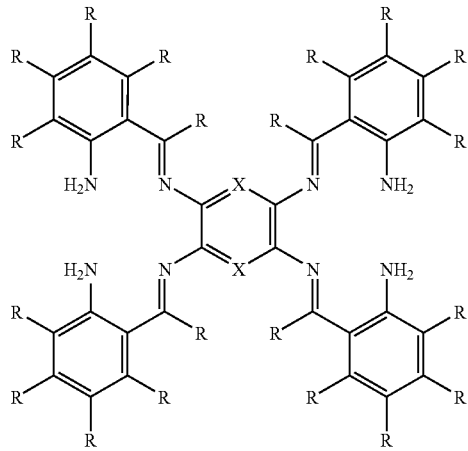

Formula (7)

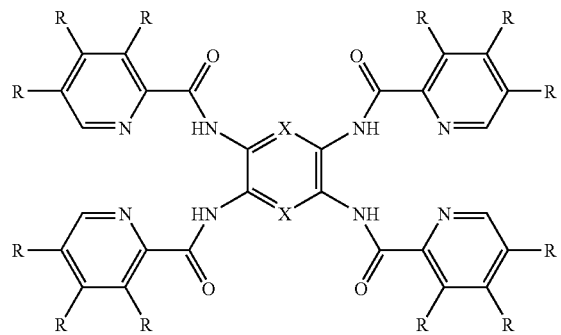

Formula (8)

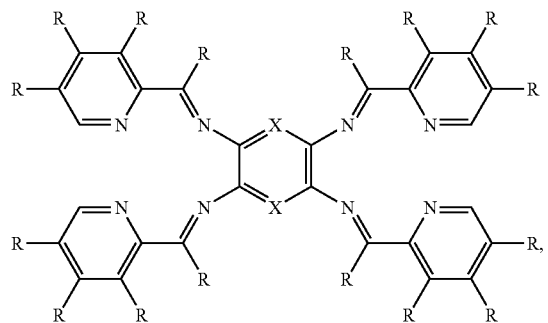

and in formulae (1) to (8), individual Rs are the same as or different from each other and are a hydrogen atom or alkyl group, and X is —CH.

2. The multidentate ligand according to claim 1, which has the two planar tetradentate coordination sites through an aromatic ring in one plane.

3. The multidentate ligand according to claim 2, wherein individual nitrogen atoms of two of the four nitrogen-containing groups are bound to the aromatic ring.

4. The multidentate ligand according to claim 2, wherein the aromatic ring is at least one of a benzene ring and a pyrazine ring.

5. The multidentate ligand according to claim 1, wherein the four nitrogen-containing groups are combined with one another to form a macrocycle.

6. The multidentate ligand according to claim 1, wherein nitrogen atoms of two of the four nitrogen-containing groups are each bound to a benzene ring.

7. The multidentate ligand according to claim 1, wherein nitrogen atoms of two of the four nitrogen-containing groups are each a nitrogen atom constituting a pyridine ring.

8. The multidentate ligand according to claim 1, wherein nitrogen atoms of two of the four nitrogen-containing groups are each bound to a carbon chain having one terminal amino group being bound to an aromatic ring.

9. The multidentate ligand according to claim 1, wherein the Ra are at least one alkyl group.

10. A multidentate ligand comprising two planar tetradentate coordination sites in one plane, wherein:

each of the planar tetradentate coordination sites contains four nitrogen-containing groups selected from among at least one of imino, amido and amino groups and has the nitrogen atoms of the four nitrogen-containing groups as coordinating atoms in one plane, and the multidentate ligand is represented by at least one of following Formulae (9) to (14):

Formula (9)

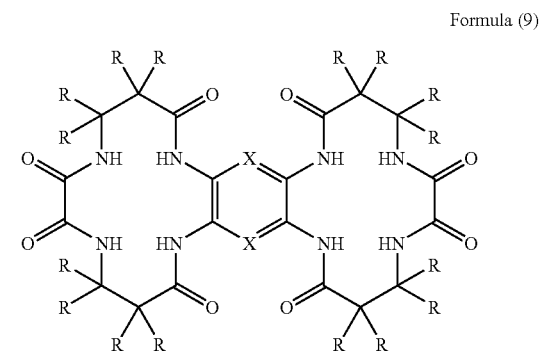

Formula (10)

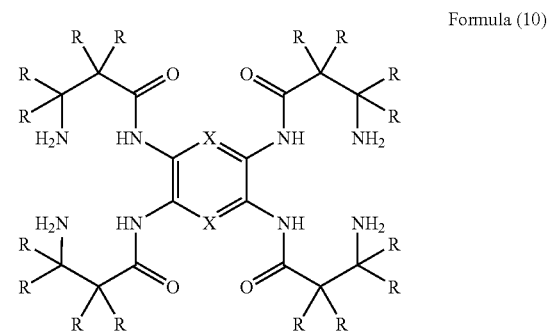

Formula (11)

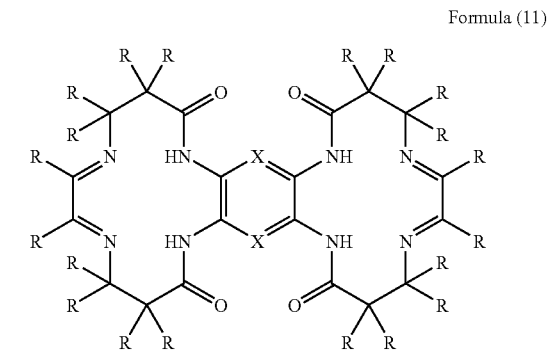

Formula (12)

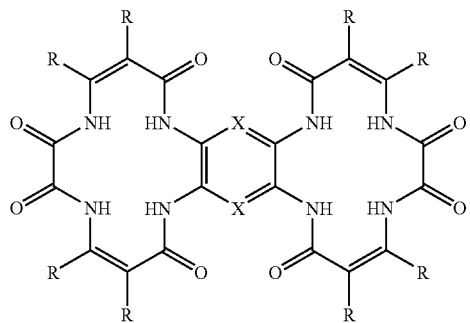

Formula (13)

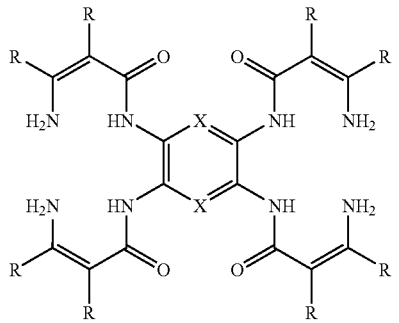

Formula (14)

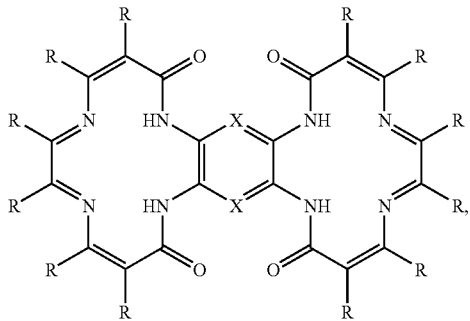

and in Formulae (9) to (14), individual Rs are the same as or different from each other and are each a hydrogen atom or an alkyl group; and X is —CH.

11. The multidentate ligand according to claim 10, wherein the Rs are at least one alkyl group.

12. The multidentate ligand according to claim 10, which has the two planar tetradentate coordination sites joined through the aromatic ring.

13. The multidentate ligand according to claim 10, wherein individual nitrogen atoms of two of the four nitrogen-containing groups are bound to the aromatic ring.

14. The multidentate ligand according to claim 10, wherein the aromatic ring is at least one of a benzene ring and a pyrazine ring.

15. The multidentate ligand according to claim 10, wherein the four nitrogen-containing groups combine to form a macrocycle.

16. The multidentate ligand according to claim 10, wherein nitrogen atoms of two of the four nitrogen-containing groups are each bound to a benzene ring.

* * * * *

UNITED STATES PATENT AND TRADEMARK OFFICE
CERTIFICATE OF CORRECTION

| | | |
|---|---|---|
| PATENT NO. | : 7,488,819 B2 | Page 1 of 1 |
| APPLICATION NO. | : 10/940648 | |
| DATED | : February 10, 2009 | |
| INVENTOR(S) | : Toshio Manabe et al. | |

It is certified that error appears in the above-identified patent and that said Letters Patent is hereby corrected as shown below:

Column 40, Line 13, change "Ra" to --Rs--.

Signed and Sealed this

Twelfth Day of May, 2009

JOHN DOLL
*Acting Director of the United States Patent and Trademark Office*